(12) United States Patent
Knight et al.

(10) Patent No.: US 12,031,003 B2
(45) Date of Patent: Jul. 9, 2024

(54) COMPOSITIONS ON PLASMA-TREATED SURFACES

(71) Applicant: Gen-Probe Incorporated, San Diego, CA (US)

(72) Inventors: Byron J. Knight, San Diego, CA (US); David Opalsky, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 746 days.

(21) Appl. No.: 17/076,448

(22) Filed: Oct. 21, 2020

(65) Prior Publication Data

US 2021/0032685 A1    Feb. 4, 2021

Related U.S. Application Data

(62) Division of application No. 15/720,467, filed on Sep. 29, 2017, now Pat. No. 10,829,810.

(60) Provisional application No. 62/402,446, filed on Sep. 30, 2016.

(51) Int. Cl.
| | |
|---|---|
| *C08J 7/048* | (2020.01) |
| *B01L 3/00* | (2006.01) |
| *C08J 7/043* | (2020.01) |
| *C08J 7/06* | (2006.01) |
| *C08J 7/12* | (2006.01) |
| *C08J 7/18* | (2006.01) |
| *C12Q 1/686* | (2018.01) |
| *G01N 3/303* | (2006.01) |

(52) U.S. Cl.
CPC ............ *C08J 7/048* (2020.01); *B01L 3/5085* (2013.01); *C08J 7/043* (2020.01); *C08J 7/065* (2013.01); *C08J 7/123* (2013.01); *C08J 7/18* (2013.01); *C12Q 1/686* (2013.01); *B01L 2200/12* (2013.01); *B01L 2200/16* (2013.01); *B01L 2300/161* (2013.01); *C08J 2345/00* (2013.01); *G01N 3/303* (2013.01)

(58) Field of Classification Search
None
See application file for complete search history.

(56) References Cited

U.S. PATENT DOCUMENTS

| | | | |
|---|---|---|---|
| 4,225,631 A | 9/1980 | Berger et al. | |
| 5,407,835 A * | 4/1995 | Adamczyk | G01N 33/9466 436/815 |

(Continued)

FOREIGN PATENT DOCUMENTS

| | | |
|---|---|---|
| CN | 101411878 A | 4/2009 |
| CN | 102387823 A | 3/2012 |

(Continued)

OTHER PUBLICATIONS

Second Office Action dated Apr. 8, 2022 in related Chinese Patent Application No. 201780059865.7 (10 pages).

(Continued)

*Primary Examiner* — Ramsey Zacharia
(74) *Attorney, Agent, or Firm* — Rothwell, Figg, Ernst & Manbeck. P.C.; Charles Cappellari; Jeffrey Landes

(57) ABSTRACT

The disclosure provides solid compositions such as lyophilisates adhered to surfaces such as plasma-treated surfaces and related methods, uses, kits, intermediates, starting materials, and downstream products.

23 Claims, 5 Drawing Sheets

(56) References Cited

U.S. PATENT DOCUMENTS

| | | | | |
|---|---|---|---|---|
| 2001/0001644 | A1* | 5/2001 | Coffman | B01L 3/5025 |
| | | | | 422/534 |
| 2002/0173016 | A1 | 11/2002 | Wurst et al. | |
| 2008/0241549 | A1 | 10/2008 | Seon et al. | |
| 2009/0011488 | A1 | 1/2009 | Zhou | |
| 2009/0081797 | A1 | 3/2009 | Fadeev et al. | |
| 2009/0305381 | A1 | 12/2009 | Bilek et al. | |
| 2011/0118138 | A1* | 5/2011 | Hill | G01N 33/9486 |
| | | | | 506/13 |
| 2012/0178091 | A1 | 7/2012 | Glezer | |
| 2013/0109030 | A1 | 5/2013 | Hardeman | |
| 2014/0271368 | A1 | 9/2014 | Hofmann | |
| 2016/0235881 | A1* | 8/2016 | Logsetty | A61L 15/26 |

FOREIGN PATENT DOCUMENTS

| | | | |
|---|---|---|---|
| JP | S58-213252 A | 12/1983 | |
| JP | S63-151857 A | 6/1988 | |
| JP | H03-22588 B2 | 3/1991 | |
| JP | 2010-538108 A | 12/2010 | |
| JP | 2014-129548 A | 7/2014 | |
| JP | 2016-067330 A | 5/2016 | |
| WO | WO-9534814 A1 * | 12/1995 | ....... G01N 33/54393 |
| WO | 2006/129656 A1 | 12/2006 | |
| WO | 2007/104107 A1 | 9/2007 | |
| WO | 2008/018399 A1 | 2/2008 | |
| WO | 2009/032117 A2 | 3/2009 | |
| WO | 2010/144682 A1 | 12/2010 | |
| WO | 2014/030005 A1 | 2/2014 | |

OTHER PUBLICATIONS

Japanese Office Action w/English translation dated Feb. 1, 2021 in related Japanese patent application No. 2019-517213 (7 pages total).

Decision of Final Rejection dated Jul. 6, 2022 in related Chinese Patent Application No. 201780059865.7 (10 pages).

Adamovich et al., "The 2017 Plasma Roadmap: Low temperature plasma science and technology", Journal of Physics D: Applied Physics, 50 (2017) 323001, https://doi.org/10.1088/1361-6463/aa76f5 (47 pages).

"Plasma-immersion ion implantation", Wikipedia, Jun. 17, 2021, https://en.wikipedia.org/w/index.php?title=Plasma-immersion_ion_implantation&oldid=1029052303 (2 pages total).

European Communication Article 94(3) dated Sep. 2, 2021 in related European Patent Application No. 17 791 491.8 (4 pages total).

Examination report No. 1 dated Aug. 26, 2021 in related Australian Patent Application No. 2017336002 (4 pages total).

Chinese Office Action and Search Report with English translation dated Jun. 30, 2021 in related Chinese Patent Application No. 201780059865.7 (15 pages total).

Japanese Pre-Appeal Examination Report with English translation dated Aug. 6, 2021 in related Japanese Patent Application No. 2019-517213 (5 pages total).

Coating. (2007). In R. E. Allen (Ed.), The penguin English Dictionary (3rd ed.). London, UK: Penguin. Retrieved from https://search.credoreference.com/content/entry/penguineng/coating/0?institutionId=743 (Year: 2007).

Coating. (2014). In Collins Dictionaries (Ed.), Collins English Dictionary (12th ed.). London, UK: Collins. Retrieved from https://search.credoreference.com/content/entry/hcengdict/coating/0?institutionId=743 (Year: 2014).

Coating. (2016). In Editors of the American Heritage Dictionaries (Ed.), The American Heritage (R) dictionary of the English language (6th ed.). Boston, MA: Houghton Mifflin. Retrieved from https://search.credoreference.com/content/entry/hmdictenglang/coating/0?institutionId=743 (Year: 2016).

Surface energy. Merriam-Webster dictionary [online]. Accessed May 22, 2019. https://www.merriam-webster.com/dictionary/surface%20energy; (Year: 2019).

Surface Energy. ScienceDirect [online]. Accessed May 22, 2019. https://www.sciencedirect.com/topics/materials-science/surface-energy (Year: 2019).

Hwang et al. "Surface modification of cyclic olefin copolymer substrates by oxygen plasma treatment". Surface & Coating Technology 202 (2008), p. 3669-3674 (Year: 2008).

Zafar et al. Drop test: A new method to measure the particle adhesion force. Powder Technology 264 (2014), p. 236-241 (Year: 2014).

AZoM. "Medical Applications of Stainless Steel 304 (UNS S30400)" (Aug. 30, 2012). Available online at https://www.azom.com/article.aspx?Article1D=6641 (Year: 2012).

PCT Partial Search Report, International Application No. PCT/US2017/054325, dated Jan. 9, 2018.

PCT International Search Report, International Application No. PCT/US2017/054325, dated Mar. 9, 2018.

PCT Written Opinion, International Application No. PCT/US2017/054325, dated Mar. 9, 2018.

European Office Action dated Apr. 28, 2020 in European Patent Application No. 17 791 491.8 (4 pages).

Japanese Office Action dated May 27, 2020 in Japanese Patent Application No. 2019-517213 with English translation (7 pages).

European Office Action dated Dec. 2, 2020 in European Patent Application No. 17 791 491.8 (5 pages).

Database WPI Week 201635, Thomson Scientific, London, GB, AN 2016-27777K & JP 2016 067330 A (Riken), May 9, 2016 (1 page).

Database WPI Week 199116, Thomson Scientific, London, GB, AN 1991-115080 & JP H03 22588 B, Mar. 27, 1991 (1 page).

Communication pursuant to Articla 94(3)EPC issued in EP 17 791 491.8 dated Oct. 10, 2023 (3 pages).

6th EP communication pursuant to Article 94(3) EPC dated May 6, 2024 in European Application No. 17791491.8 (3 pages).

* cited by examiner

COMPOSITIONS ON PLASMA-TREATED SURFACES

CROSS-REFERENCE TO RELATED APPLICATIONS

This application claims the benefit under 35 U.S.C. §§ 120, 121 of the filing date of non-provisional patent application Ser. No. 15/720,467 filed Sep. 29, 2017, now U.S. Pat. No. 10,829,810, which claims the benefit of priority under 35 U.S.C § 119(e) to provisional application No. 62/402,446, filed Sep. 30, 2016; the entire contents of which are incorporated herein by reference

INTRODUCTION AND SUMMARY

Solid compositions do not necessarily adhere strongly to surfaces. Lack of sufficient adhesion can be a problem in areas such as providing solid pharmaceutical compositions or reagents for performing chemical, pharmaceutical, or biochemical reactions or assays, in that the composition may become dislocated or loose during shipment or handling. Dislocated or loose compositions may complicate or prevent reconstitution, such as where a fixed volume of reconstitution liquid is dispensed in an instrument and some or all of the composition is no longer adhered at or near the bottom of the vessel in which reconstitution occurs. Failure to completely reconstitute the composition into a liquid state can adversely affect assay performance.

Compositions, e.g., comprising bulking reagents or reagents for performing chemical or biochemical reactions or assays, are provided as solid compositions adhered to a plasma-treated surfaces. It has been found that plasma treatment of a surface can improve the adhesion to the surface of solid compositions formed by drying a liquid solution, and that plasma treatment can prevent or reduce the frequency of dislocation or loosening of solid compositions from a surface, such as the surface at or near the bottom of a vessel. Without wishing to be bound to a particular theory, plasma treatment may increase the hydrophilicity of the surface and therefore its wettability, strengthening the interaction of the reagent with the surface, and that the strengthened interaction persists following a drying process, e.g., lyophilization.

The present disclosure is premised in part on the insight that the adhesion of a solid composition such as a lyophilized pellet to a surface such as a plastic can be strengthened by plasma treatment of the surface before the solid composition is in contact with the surface. Accordingly, the compositions, methods, and kits disclosed herein can provide products with improved ability to survive agitation that may occur during processes such as shipping and handling, or at least provide the public with a useful choice.

Accordingly, disclosed herein is a method of preparing a solid composition adhered to a plasma-treated surface, the method comprising drying a solution on the plasma-treated surface and forming a solid composition from the solution, the solid composition being adhered to the plasma-treated surface.

In some embodiments, the plasma-treated surface is a surface treated with a cold cathode discharge, hollow cathode discharge, DC-induced discharge, radio frequency (RF)-induced discharge, corona discharge, glow discharge, or charged particle beam. In some embodiments, the plasma-treated surface is a corona-discharge-treated surface. In some embodiments, the method comprises preparing the plasma-treated surface by treating a surface with a corona discharge at a watt density ranging from about 25 watt/min/$m^2$ to about 2000 watt/min/$m^2$, about 50 watt/min/$m^2$ to about 1500 watt/min/$m^2$, about 100 to about 1200 watt/min/$m^2$, about 200 to about 1000 watt/min/$m^2$, about 100 to about 600 watt/min/$m^2$, or about 200 watt/min/$m^2$ to about 600 watt/min/$m^2$. In some embodiments, the surface was treated with a corona discharge at a watt density ranging from about 25 watt/min/$m^2$ to about 2000 watt/min/$m^2$, about 50 watt/min/$m^2$ to about 1500 watt/min/$m^2$, about 100 to about 1200 watt/min/$m^2$, about 200 to about 1000 watt/min/$m^2$, about 100 to about 600 watt/min/$m^2$, or about 200 watt/min/$m^2$ to about 600 watt/min/$m^2$. In some embodiments, (i) the plasma-treated surface has a surface energy ranging from about 33 to about 45 dynes/cm, from about 35 to about 42 dynes/cm, or from about 37 to about 40 dynes/cm, optionally wherein the surface comprises a polyolefin; or (ii) the plasma-treated surface has a surface energy ranging from about 35 to about 55 dynes/cm, from about 37 to about 53 dynes/cm, or from about 40 to about 50 dynes/cm, optionally wherein the surface comprises a polyethylene or polypropylene. In some embodiments, the plasma-treated surface has a surface energy increase relative to an untreated surface of the same composition, the surface energy increase ranging from about 3 to about 20 dynes/cm, about 4 to about 15 dynes/cm, about 5 to about 12 dynes/cm, or about 6 to about 10 dynes/cm.

In some embodiments, the drying comprises at least one of evaporating, dehydrating, desiccating, lyophilizing, sublimation, and spray-drying. In some embodiments, the solution is frozen during at least part of the drying step. In some embodiments, the drying comprises lyophilizing. In some embodiments, the solution is liquid during at least part of the drying step. In some embodiments, the drying occurs under vacuum. In some embodiments, the drying occurs at a temperature greater than about 30° C. In some embodiments, the solution, prior to drying, has a volume ranging from about 5 µl to about 20 ml, about 200 µl to about 20 ml, about 1 ml to about 20 ml, about 5 ml to about 20 ml, about 5 µl to about 1 ml, about 5 µl to about 500 µl, about 5 µl to about 200 µl, about 5 µl to about 100 µl, about 5 µl to about about 5 µl to about 20 about 5 µl to about 10 about 10 µl to about 200 about 20 µl to about 200 µl, about 50 µl to about 200 µl, or about 100 µl to about 200 µl.

In some embodiments, the plasma-treated surface is the interior surface of a plasma-treated vessel. In some embodiments, the plasma-treated surface comprises plastic. In some embodiments, the plastic comprises at least one of a polyethylene, polyethylene terephtualate, polypropylene, polymethacrylate, polyvinyl chloride, polystyrene, polyolefin, polycarbonate, polyurethane, starch-derived plastic, or cyclic olefin copolymer. In some embodiments, wherein the plastic comprises a cyclic olefin copolymer.

In some embodiments, the solution comprises water. In some embodiments, the solution comprises a polar organic solvent. In some embodiments, the polar organic solvent comprises at least one of ethanol, isopropanol, DMSO, or glycerol. In some embodiments, the solution comprises a non-polar organic solvent.

In some embodiments, the solution comprises a bulking agent. In some embodiments, the bulking agent comprises a saccharide. In some embodiments, the bulking agent comprises at least one of sucrose, mannitol, glycine, hydroxyethyl starch, raffinose, or trehalose, or alternatively wherein the bulking agent is a saccharide selected from sucrose, mannitol, raffinose, or trehalose.

In some embodiments, the solution comprises one or more enzymes. In some embodiments, the one or more enzymes include at least one of a DNA polymerase, an RNA polymerase, a ligase, a kinase, a phosphatase, a protease, an exonuclease, and an endonuclease. In some embodiments, the one or more enzymes include a thermostable DNA polymerase. In some embodiments, the thermostable DNA polymerase is a hot-start thermostable DNA polymerase or is complexed with an antibody. In some embodiments, the one or more enzymes include a DNA-dependent polymerase, reverse transcriptase or other enzyme that is present in the solution at a concentration from about 0.20 U/µl to about 0.72 U/µl or from about 0.1 U/µl to about 0.6 U/µl.

In some embodiments, the solution comprises a buffer. In some embodiments, the buffer is an organic buffer.

In some embodiments, the solution has an inorganic salt concentration of about 5 mM or less. In some embodiments, the solution is free of inorganic salt. In some embodiments, the solution comprises a salt.

In some embodiments, the solution comprises at least one oligonucleotide useful for performing a molecular assay. In some embodiments, the at least one oligonucleotide is selected from an amplification oligomer and a probe. In some embodiments, the oligonucleotide comprises a label. In some embodiments, the label is a fluorescent, chemiluminescent, affinity, or radioactive label.

In some embodiments, the solution comprises one or more nucleoside triphosphates. In some embodiments, the solution comprises one or more deoxynucleoside triphosphates. In some embodiments, the solution comprises dATP, dGTP, dCTP, and at least one of dTTP and dUTP. In some embodiments, at least one of the one or more nucleoside triphosphates is present in an amount ranging from about 0.1 mM to about 0.3 mM or from about 0.2 mM to about 0.6 mM in the solution. In some embodiments, the solution comprises at least one probe selected from a capture probe and a hydrolysis probe.

In some embodiments, the solution comprises an RNase inhibitor. In some embodiments, the RNase inhibitor is present in the solution at a concentration from about 0.12 U/µl to about 0.20 U/µl.

In some embodiments, the solution comprises a chelating agent. In some embodiments, the chelating agent is EDTA, EDDS, or MGDA. In some embodiments, the chelating agent is present in the solution at a concentration from about 1.5 mM to about 2.0 mM.

In some embodiments, the solution comprises a detergent. In some embodiments, the detergent is a nonionic, cationic, anionic, or zwitterionic detergent.

In some embodiments, the solution contains a single unit dose of amplification reagents. In some embodiments, the solution contains a single unit dose of detection reagents. In some embodiments, the solution contains a pharmaceutically active agent.

In some embodiments, a method comprises, before a drying step, dispensing a solution onto a plasma-treated surface. In some embodiments, a method comprises, before a dispensing step, plasma-treating a surface to form a plasma-treated surface. In some embodiments, a method comprises, after a drying step, sealing a solid composition in a vessel comprising a plasma-treated surface.

Also provided is a cyclic olefin copolymer surface containing a liquid or frozen solution in a concavity of the cyclic olefin copolymer surface, wherein the cyclic olefin copolymer surface has a surface energy from about 35 dynes/cm to about 55 dynes/cm or a contact angle of about 5° to about 50°, and the liquid or frozen solution comprises a saccharide.

In some embodiments, the liquid or frozen solution comprises water. In some embodiments, the liquid or frozen solution comprises a polar organic solvent. In some embodiments, the polar organic solvent comprises at least one of ethanol, isopropanol, DMSO, or glycerol. In some embodiments, the liquid or frozen solution comprises a non-polar organic solvent.

In some embodiments, the liquid or frozen solution comprises one or more enzymes. In some embodiments, the one or more enzymes include at least one of a DNA polymerase, an RNA polymerase, a ligase, a kinase, a phosphatase, a protease, an exonuclease, and an endonuclease.

In some embodiments, the liquid or frozen solution comprises a buffer. In some embodiments, the liquid or frozen solution is free of inorganic salt or has an inorganic salt concentration of about 5 mM or less. In some embodiments, the liquid or frozen solution comprises a salt.

In some embodiments, the liquid or frozen solution comprises at least one oligonucleotide useful for performing a molecular assay. In some embodiments, the liquid or frozen solution comprises one or more nucleoside triphosphates.

In some embodiments, the solution is liquid. In some embodiments, the solution is frozen.

Also provided is a solid composition adhered to a plasma-treated cyclic olefin copolymer surface, wherein the solid composition is within a concavity of the cyclic olefin copolymer surface, the concavity having a wall angle from about 90 degrees to about 60 degrees, the solid composition having a mass from about 600 micrograms to about 100 mg and comprising a saccharide, and wherein the solid composition is sufficiently adhered to remain substantially attached to the cyclic olefin copolymer surface following a package performance test in which the cyclic olefin copolymer surface containing the solid composition is dropped from a height of up to about 480 mm onto a stainless steel surface. Also provided is a solid composition adhered to a plasma-treated surface, wherein the solid composition adhered to the plasma-treated surface is produced by a method disclosed herein. Also provided is a solid composition adhered to a plasma-treated surface, wherein the solid composition comprises a bulking agent and at least one of an enzyme and an oligonucleotide.

In some embodiments, the plasma-treated surface comprises plastic. In some embodiments, the plastic comprises at least one of a polyethylene, polyethylene terephthalate, polypropylene, polymethacrylate, polyvinyl chloride, polystyrene, polyolefin, polycarbonate, polyurethane, starch-derived plastic, or cyclic olefin copolymer. In some embodiments, the plastic comprises a cyclic olefin copolymer.

In some embodiments, the bulking agent comprises a saccharide, glycine, or hydroxyethyl starch. In some embodiments, the saccharide comprises at least one of sucrose, mannitol, raffinose, or trehalose. In some embodiments, the solid composition is within a vessel comprising the plasma-treated surface.

In some embodiments, the vessel comprises a tube having a volume ranging from about 10 µl to about 60 ml. In some embodiments, the vessel is a multiwell plate comprising a plurality of wells.

In some embodiments, the solid composition has a mass ranging from about 5 mg to about 20 g, about 200 mg to about 20 g, about 1 g to about 20 g, about 5 g to about 20 g, about 5 mg to about 1 g, about 5 mg to about 500 mg, about 5 mg to about 200 mg, about 5 mg to about 100 mg, about 5 mg to about 50 mg, about 5 mg to about 20 mg, about 5 mg to about 10 mg, about 10 mg to about 200 mg, about 20 mg to about 200 mg, about 50 mg to about 200 mg, or about 100 mg to about 200 mg.

In some embodiments, the solid composition comprises one or more enzymes. In some embodiments, the one or more enzymes include at least one of a DNA polymerase, an RNA polymerase, a ligase, a kinase, a phosphatase, a protease, an exonuclease, and an endonuclease.

In some embodiments, the solid composition comprises a buffer. In some embodiments, the solid composition comprises a salt. In some embodiments, the solid composition is free of inorganic salt or has an inorganic salt concentration of about 5 mM or less.

In some embodiments, the solid composition comprises at least one oligonucleotide useful for performing a molecular assay. In some embodiments, the solid composition comprises one or more nucleoside triphosphates. In some embodiments, the solid composition contains a single unit dose of amplification or detection reagents. In some embodiments, the solid composition contains a pharmaceutically active agent.

Also provided is a kit comprising a reconstitution liquid and a solid composition of disclosed herein. Also provided is a method of forming a mixture, the method comprising forming a reconstituted composition by combining a reconstitution liquid and a solid composition disclosed herein.

In some embodiments, the reconstitution liquid comprises at least one of water, a polar organic solvent, and a nonpolar organic solvent. In some embodiments, the reconstitution liquid comprises water. In some embodiments, the reconstitution liquid comprises at least one inorganic salt.

In some embodiments, a method disclosed herein further comprises adding a nucleic acid, wherein the nucleic acid undergoes at least one nucleic acid modification or hybridization reaction. In some embodiments, the nucleic acid modification or hybridization reaction comprises nucleic acid synthesis or amplification. In some embodiments, the nucleic acid modification or hybridization reaction comprises hybridizing a probe to the nucleic acid to form a hybridized complex.

In some embodiments, a method disclosed herein further comprises detecting the hybridized complex or nucleolysis of the probe.

Section headings are provided for the convenience of the reader and are not to be construed as limiting the disclosure.

BRIEF DESCRIPTIONS OF THE FIGURES

DETAILED DESCRIPTION

Definitions

Before describing the present teachings in detail, it is to be understood that the disclosure is not limited to specific compositions or process steps, as such may vary. It should be noted that, as used in this specification and the appended claims, the singular form "a", "an" and "the" include plural references unless the context clearly dictates otherwise. Thus, for example, reference to "a bulking agent" includes a plurality of bulking agents and the like.

It will be appreciated that there is an implied "about" prior to the temperatures, concentrations, times, etc. discussed in the present disclosure, such that slight and insubstantial deviations are within the scope of the present teachings herein. In general, the term "about" indicates insubstantial variation in a quantity of a component of a composition not having any significant effect on the activity or stability of the composition. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

As used herein, material is considered "adhered" to a surface if it does not visibly move relative to the surface when the surface is agitated, e.g., shaken (e.g., by hand at a frequency of about 1-3 Hz) or inverted.

A "bulking agent" provides a matrix for the deposit of proteins and other reagents during drying and storage. (Carpenter et al (2002) Rational design of stable lyophilized protein formulations. Kluwer Academic/Plenum, New York, pp. 109-133). Bulking agents can be used to form a product "cake" or other structure, can prevent protein or other reagents from being lost from the vessel during drying, and can increase protein stability.

A chelating agent is an agent that sequesters divalent ions, such as $Mg^{2+}$ or $Mn^{2+}$, that may be required for activity of certain enzymes.

A "concavity" is a depression, well, indentation, or other feature of a surface that is suitable for holding a solution or solid composition formed from the solution.

Figure 1:
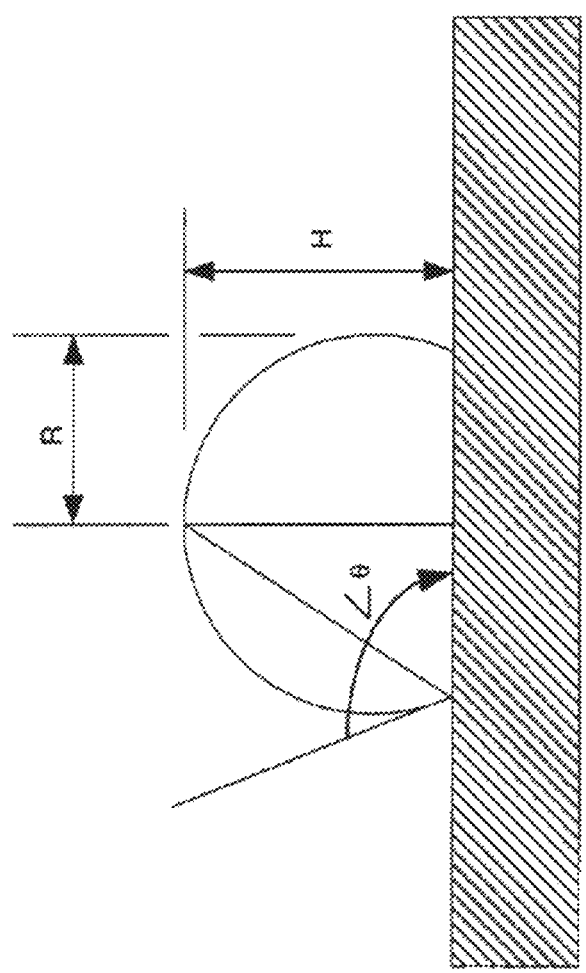
FIG. 1 is an illustration of contact angle measurement in which θ is the contact angle, H is droplet height, and R is half of the droplet width.

A "contact angle" is the angle between a surface of a substrate and the tangent line drawn at the three-phase point to the surface of droplet of liquid on the substrate. See FIG. 1. A contact angle θ can be calculated according to the formula $\theta=2(\arctan(H/R))$ where H is the droplet height and R is half of the droplet width. Unless otherwise indicated, the droplet is water for contact angles referred to herein. Contact angle measurement is discussed in detail in ASTM International Standard D 5946-04, "Standard Test Method for Corona-Treated Polymer Films Using Water Contact Angle Measurements" (2004). See also U.S. Pat. No. 5,268,733 for discussion of contact angle measurement methods and equipment. Unless otherwise indicated, contact angle measurement is performed using a droplet of water. As used herein, a surface is considered to have a contact angle of a certain value or in a certain range if that contact angle is observed when the surface is contacted with water.

As used herein, "first," "second," etc. are used with reference to elements of a structure, composition, or method without any implication as to the ordering or positioning of the elements; thus a "first" element may be anterior, overlapping, posterior, above, below, before, simultaneous with, or after a "second" element unless one of ordinary skill in the art would understand otherwise from the context.

The terms "lyophilization," "lyophilized," and "freeze-dried" refer to a process by which the material to be dried is first frozen and then the ice or frozen solvent is removed by sublimation in a vacuum environment. "Lyophilisate" refers to a lyophilized substance.

The term "stringent" in reference to nucleic acid hybridization (including "stringent hybridization conditions" or "stringent conditions") refers to conditions where a specific oligonucleotide is able to hybridize with target nucleic acids over other nucleic acids present in the test sample. It will be appreciated that these conditions may vary depending upon factors including the GC content and length of the oligonucleotide, the hybridization temperature, the composition of the hybridization reagent or solution, and the degree of hybridization specificity sought. Appropriate hybridization conditions are well known in the art for probes, amplification oligonucleotides, target capture oligonucleotides, blockers and other oligonucleotides, may be predicted based on sequence composition, or can be determined by using routine testing methods (e.g., Sambrook et al., *Molecular Cloning, A Laboratory Manual*, 2nd ed. (Cold Spring Harbor Laboratory Press, Cold Spring Harbor, NY, 1989) at §§ 1.90-1.91, 7.37-7.57, 9.47-9.51 and 11.47-11.57, particularly §§ 9.50-9.51, 11.12-11.13, 11.45-11.47 and 11.55-11.57).

An amplification oligomer is a primer or promoter-primer that can support template-dependent replication. An amplication oligomer pair is a pair of such oligomers that support template dependent replication of opposing strands of a template. Multiplex amplification is amplification peformed with multiple amplification oligomer pairs simultaneously.

A probe is an oligonucleotide that can hybridize to an amplification product to reveal presence or amount of the amplifcation product. Such probes often incorporate a molecule giving a fluorescent or other detectable signal in which case they are referred to as detectably labelled probes.

A primer-probe set is a combination of primers and probe configured for generating and detecting an amplification product from a template nucleic acid.

"Reconstitution time" is the time that is required to rehydrate a dried formulation with a solution to result in a solution that is free of particles or turbidity to the naked eye.

A "single unit dose" or "SUD" refers to a quantity of reagents that is used to perform an assay on a single sample. A single unit dose can be a solution. By way of example, a single unit dose can be a dried pellet containing reagents useful for the amplification of a single sample in a single vessel.

As used herein, "or" is used inclusively, i.e., equivalent to "and/or," unless clearly indicated to the contrary, such as in the expression "no more than one of A or B."

The terms "or combinations thereof," "at least one of," and "one or more of" as used herein refer to all permutations and combinations of the listed terms preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, also included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

A "package performance test" refers to a test in which a surface (e.g., of a vessel) to which a solid composition is adhered is dropped from a certain height (e.g., about 480 mm) onto a substrate (e.g., stainless steel) to determine the extent of adhesion of the solid composition to the surface. The solid composition is considered to remain substantially attached when no visible part or less than about 10% or about 5% by volume of the solid composition becomes loose (e.g., moves relative to the surface when the surface is shaken or inverted). In some embodiments, the height used in the package performance test is a height ranging from about 20 mm to 1000 mm, e.g., about 20 mm, about 40 mm, about 60 mm, about 80 mm, about 100 mm, about 120 mm, about 140 mm, about 160 mm, about 180 mm, about 200 mm, about 220 mm, about 240 mm, about 260 mm, about 280 mm, about 300 mm, about 320 mm, about 340 mm, about 360 mm, about 380 mm, about 400 mm, about 420 mm, about 440 mm, about 460 mm, about 480 mm, about 500 mm, about 520 mm, about 540 mm, about 560 mm, about 580 mm, about 600 mm, about 620 mm, about 640 mm, about 660 mm, about 680 mm, about 700 mm, about 720 mm, about 740 mm, about 760 mm, about 780 mm, about 800 mm, about 820 mm, about 840 mm, about 860 mm, about 880 mm, about 900 mm, about 920 mm, about 940 mm, about 960 mm, about 980 mm, or about 1000 mm; or about 20 mm to about 60 mm, about 60 mm to about 100 mm, about 100 mm to about 200 mm, about 200 mm to about 300 mm, about 300 mm to about 400 mm, about 500 mm to about 600 mm, about 600 mm to about 700 mm, about 800 mm to about 900 mm, or about 900 mm to about 1000 mm. In some embodiments, the substrate is a soft foam, e.g., polyurethane, such as a polyurethane sheet. In some embodiments, the substrate is a firm cushion or mat material, such as Ensolite® AF having a compression resistance range from about 18 to about 20 lbs/in$^2$. In some embodiments, the substrate is a hard surface, such as stainless steel. In some embodiments, the substrate has a thickness of about 1 cm, 2 cm, 3 cm, 4 cm, or 5 cm.

"Plasma" is a state of matter in which positive and negative charged particles are unbound, and which does not have a definite shape or definite volume unless enclosed in a container. A plasma can also contain uncharged particles that would be a gas in the absence of charged particles, e.g., air, $O_2$, $N_2$, etc. A plasma can be produced by applying an electric field to a gas, as in the case of corona discharges. Other methods of producing plasma include heating a gas, electromagnetic radiation (e.g., radio frequency (RF)-induced discharge), and generating a charged particle beam, such as an electron beam.

A surface is "plasma-treated" if it has been exposed to plasma and has at least one property affected by the exposure, e.g., a reduced contact angle, increased surface energy, or increased degree of adhesion to a solid composition, relative to an untreated counterpart.

A "saccharide" is a compound containing carbon, hydrogen, and oxygen in which the ratio of oxygens to carbons is about (but not necessarily exactly) 1:1 and the ratio of hydrogens to oxygens is about 2:1 (but not necessarily exactly). Saccharides include sugar alcohols such as xylitol ($C_5H_{12}O_5$) as well as sugars such as glucose ($C_6H_{12}O_6$) and sucrose ($C_{12}H_{22}O_{11}$).

As used herein, a "solid composition" refers to non-flowable matter. Unless otherwise indicated, solid compositions do not refer to coatings, such as dried paint, which are generally thin in one dimension relative to other dimensions. Solid compositions include lyophilizates, pellets, etc., that result from drying a solution in a way that gives a non-coating residue. Solid compositions commonly are crystalline or have a lattice structure at the molecular level, although solid compositions also include amorphous and quasicrystalline solids. Solid compositions do not include frozen solutions that would not be solid at 20° C. and 1 atm pressure. In some embodiments, solid compositions are macroscopic in three orthogonal dimensions (e.g., they have a length, width, and height observable without aid of a microscope, e.g., greater than about 1 mm). Solid compositions herein generally have a density in the range of about 0.5 to about 2 g/cm$^3$ and their volume can be estimated accordingly.

As used herein, a "solution" is a composition comprising a solvent and a solute dissolved therein, and includes not only liquid solutions but also frozen solutions, e.g., the result of freezing a solvent containing a dissolved solute such that the solute remains generally disperse within the frozen solvent (as opposed to precipitating out or otherwise forming an observably different solid phase from the solvent).

Exemplary Methods, Compositions, and Kits

In some embodiments, methods are provided for preparing an adhered solid composition, in which a solution is dried on a plasma-treated surface, forming the solid composition, which is adhered to the plasma-treated surface. In some embodiments, the plasma-treated surface is a surface treated with a cold cathode discharge, hollow cathode discharge, DC-induced discharge, radio frequency (RF)-induced discharge, corona discharge, glow discharge, or charged particle beam. In some embodiments, the plasma-treated surface is a surface treated with a corona discharge.

In some embodiments, a solid composition adhered to a plasma-treated surface is provided. In some embodiments, provided is a cyclic olefin copolymer surface comprising at least one concavity with a wall angle from about 90 degrees to about 60 degrees, wherein the cyclic olefin copolymer surface contains a solid composition having a mass from about 600 micrograms to about 100 mg and comprising a saccharide, wherein the solid composition is attached to the cyclic olefin copolymer surface, and wherein the solid composition remains substantially attached to the cyclic olefin copolymer surface following a package performance test whereby the cyclic olefin copolymer surface containing the solid composition is dropped from a height of about 480 mm onto a stainless steel surface. In some embodiments, provided is a solid composition adhered to a plasma-treated surface, wherein the solid composition comprises a bulking agent and at least one of an enzyme and an oligonucleotide. In some embodiments, provided is a solid composition adhered to the plasma-treated surface that is produced by a method disclosed herein.

Also provided is a kit comprising a solid composition disclosed herein, such as a solid composition adhered to a plasma-treated surface, the kit optionally further comprising a reconstitution liquid.

Also provided is a method of forming a mixture, the method comprising forming a reconstituted composition by combining a reconstitution liquid and a solid composition disclosed herein, such as a solid composition adhered to a plasma-treated surface.

In some embodiments, a cyclic olefin copolymer surface containing a liquid or frozen solution in a concavity of the cyclic olefin copolymer surface is provided, wherein the cyclic olefin copolymer has a decreased contact angle or increased surface energy relative to cyclic olefin copolymer not treated with plasma. In some embodiments, a cyclic olefin copolymer surface containing a liquid or frozen solution in a concavity of the cyclic olefin copolymer surface is provided, wherein the cyclic olefin copolymer has a surface energy from about 35 dynes/cm to about 55 dynes/cm or a contact angle of about 5° to about 50°.

The details of certain embodiments provided herein, whether in the following paragraphs, the introduction and summary, the drawings and descriptions thereof, the examples, the claims (which are considered part of this specification) or any other part of this application, are described with respect to any and all of the methods, compositions, and kits disclosed herein to which they can apply according to the understanding of one skilled in the art.

Treatment of the surface with plasma is believed to increase the extent to which the surface interacts favorably with molecules of the solid composition as it forms during drying of a solution. For example, plasma treatment may increase the charge density or the density of partially charged atoms or groups in the surface, which are capable of noncovalent interactions such as dipole-dipole, hydrogen bonding, etc. with molecules of the solid composition. Accordingly, a range of durations and intensities of plasma treatment can be used, e.g., treatment with a plasma source such as a corona discharge discharge at a watt density ranging from about 25 watt/min/m$^2$ to about 2000 watt/min/m$^2$, about 50 watt/min/m$^2$ to about 1500 watt/min/m$^2$, about 100 to about 1200 watt/min/m$^2$, about 200 to about 1000 watt/min/m$^2$, about 100 to about 600 watt/min/m$^2$, or about 200 watt/min/m$^2$ to about 600 watt/min/m$^2$.

The extent of plasma-treatment can also be expressed in terms of surface energy or a change in surface energy. In some embodiments, the plasma-treated surface, such as a surface comprising a polyolefin, has a surface energy ranging from about 33 to about 45 dynes/cm, from about 35 to about 42 dynes/cm, or from about 37 to about 40 dynes/cm. In some embodiments, the plasma-treated surface, such as a surface comprising a polyethylene or polypropylene, has a surface energy ranging from about 35 to about 55 dynes/cm, from about 37 to about 53 dynes/cm, or from about 40 to about 50 dynes/cm. In some embodiments, the plasma-treated surface has a surface energy increase relative to an untreated surface of the same composition, with the surface energy increase ranging from about 3 to about 20 dynes/cm, about 4 to about 15 dynes/cm, about 5 to about 12 dynes/cm, or about 6 to about 10 dynes/cm.

The extent of plasma-treatment can also be expressed in terms of contact angle or a change in contact angle. In some embodiments, the plasma-treated surface, such as a surface comprising a polyolefin, has a contact angle of about 5° to about 50°, e.g., about 5° to about 40°, about 5° to about 30°, about 5° to about 10°, about 10° to about 20°, about 10° to about 30°, about 10° to about 40°, about 20° to about 30°, about 30° to about 40°, or about 40° to about 50°. In some embodiments, the contact angle is about 5° to about 25°. In some embodiments, the contact angle is about 10° to about 25°. In some embodiments, the contact angle is decreased relative to the contact angle of the surface before plasma treatment. The amount of the decrease is in some embodiments a value ranging from about 30° to about 95°, e.g., about 40° to about 90°, about 30° to about 40°, about 40° to about 50°, about 50° to about 60°, about 60° to about 70°, about 70° to about 80°, about 80° to about 90°, or about 90° to about 95°.

In some embodiments, the plasma-treated surface is the interior surface of a plasma-treated vessel, e.g., a tube, or multiwell plate or cartridge. In some embodiments, the surface or vessel comprises plastic. In some embodiments, the plastic comprises at least one of a polyethylene, polyethylene terephtalate, polypropylene, polymethacrylate, polyvinyl chloride, polystyrene, polyolefin, polycarbonate, polyurethane, starch-derived plastic, or cyclic olefin copolymer.

Equipment for plasma treatment, methods of using such equipment, or general discussion of plasma treatment can be found, e.g., in WO2002/023960 A1; US2009/0143718 A1; U.S. Pat. Nos. 6,106,653; 7,556,845 B2; 3,870,610; US2013/0017672 A1; U.S. Pat. Nos. 8,361,565 B2; and 9,005,188 B2. It is believed that plasma treatment has not been applied in the context of adhesion of solid compositions such as lyophilisates to surfaces. Nonetheless, in view of the guidance of this disclosure and the available knowledge regarding plasma treatment in general, one skilled in the art can fully practice, make, and use the compositions and methods disclosed herein.

In some embodiments, drying comprises lyophilizing. In some embodiments, the solid composition is a lyophilisate, such as a lyophilized pellet. In some embodiments, drying comprises at least one of evaporating, dehydrating, desiccating, lyophilizing, and spray-drying. In some embodiments, the drying occurs under vacuum, e.g., a pressure less than or equal to about 0.9, 0.8, 0.7, 0.6, 0.5, 0.4, 0.3, 0.2, 0.1, 0.05, or 0.01 atmospheres, or a pressure than or equal to about 0.9, 0.8, 0.7, 0.6, 0.5, 0.4, 0.3, 0.2, 0.1, 0.05, or 0.01 times ambient pressure. In some embodiments, the drying occurs at increased temperature, e.g., a temperature higher than about 1, 2, 3, 4, or 5° C. higher than ambient temperature or greater than about 30° C., such as about 30° C. to 110° C., about 30° C. to 40° C., about 40° C. to 50° C., about 50° C. to 60° C., about 60° C. to 70° C., about 70° C. to 80° C., about 80° C. to 90° C., about 90° C. to 100° C., or about 100° C. to 110° C. In some embodiments, the drying occurs at ambient temperature or a temperature from about 15° C. to 30° C., about 15° C. to 25° C., about 20° C. to 30° C., about 15° C. to 20° C., about 20° C. to 25° C., or about 25° C. to 30° C. In some embodiments, the drying occurs at reduced temperature, e.g., a temperature lower than about 1, 2, 3, 4, or 5° C. lower than ambient temperature or lower than 15° C., such as about 10° C. to about 15° C., about 5° C. to about 10° C., about 0° C. to about 5° C., about −5° C. to about 0° C., about −10° C. to about 0° C., about −20° C. to about −10° C., about −30° C. to about −20° C., about −40° C. to about −30° C., about −50° C. to about −40° C., about −60° C. to about −50° C., about −70° C. to about −60° C., about −80° C. to about −70° C., about −90° C. to about −80° C., or about −100° C. to about −90° C.

In some embodiments, the solution is frozen during at least part of the drying step. In some embodiments, the solution is liquid during at least part of the drying step. In some embodiments, the solution is frozen during all or substantially all of the drying step. In some embodiments, the solution is liquid during all or substantially all of the drying step. In some embodiments, the solution is liquid during part of the drying step and solid during at least part of the drying step, such as when part of the solvent undergoes a liquid to gas transition, e.g., during evaporation, followed by freezing, and then remaining solvent undergoes a solid to gas transition as in sublimation, e.g., during lyophilization.

Solutions can be can be lyophilized using standard methods and equipment. Freeze driers are available from, e.g., GEA Process Engineering, Columbia, MD Contract freeze drying services are provided by, e.g., Biopharma Technology Ltd., Winchester, Hampshire, Great Britain and by BioPharma Solutions Sterile Contract Manufacturing, Baxter Healthcare Corp, Deerfield, IL Guidance for lyophilization is available from, e.g., L. Rey, J. C. May (eds.) (2010) Freeze Drying/Lyophilization of Pharmaceuticals and Biological Products, 3$^{rd}$. ed. Informa Healthcare, NY or Methods in Enzymology, Vol. 22, Pages 33-39, Academic Press, New York (1971); or Freeze-Drying, E. W. Flosdorf, Rheinhold, New York (1949). Optionally, oxygen content can be reduced during freeze-drying (Phillips et al (2001) Biologics. 19:219).

A variety of containers are suitable for drying. A container should be able to withstand the outside pressure when the container is sealed and stored under partial vacuum. The container should be made of a material that allows a reasonable transfer of heat from outside to inside. The size of the container is preferably such that the solution to be dried occupies not more than 20% of the total volume to avoid overflow.

Samples can be dried in separate vessels or a multispecimen vessels. A multi-specimen vessel means a contiguous vessel that can contain at least two specimens such that they can be stored and manipulated in parallel but separately. Standard formats for multispecimen vessels, e.g., multiwell plates or cartridges, include formats having 6, 24, 96, 384 or 1536 concavities, e.g., wells. The volume of each well in an example of a 96 well format is about 300-400 microliters with a working volume of about 75-200 microliters. Volumes generally vary inversely with the number of wells, typically in a range between 1 nL and 10 mL for each well, although other sizes are also contemplated. Exemplary wells and concavities can have flat bottoms, round bottoms, or V-shaped bottoms among others. In addition, wells are sometimes further referred to as reaction wells. The term reaction well does not require that any reaction actually take place in the reaction well. Rather, the term is used to refer to a vessel or well that contains a reagent, and that may have no reaction therein, a partial reaction therein, or a full reaction therein.

As discussed above, a multiwell plate, in some embodiments herein, can undergo lyophilization to form a solid composition from a solution. Lyophilization may occur in a nest device (see copending International Application No. PCT/US2016/045166). A nest is a container for the plate with vents which can be closed by a mechanism operable from outside a sealed lyophilization chamber. The nest containing the multiwell plate is placed within a lyophilization chamber with the one or more vents in the open position. The chamber is then sealed and a lyophilization atmosphere is applied throughout the chamber including the space within the nest. The one or more vents are then closed, thereby sealing the nest. The seal on the lyophilization chamber is later released and the nest containing the multiwell plate is removed. The nest may then be relocated and stored with the multiwell plate positioned therein until an operator is ready to use the lyophilized composition located therein or to reseal the multiwell plate containing the lyophilized specimens for further storage or sale. The wells of the multiwell plate can then be sealed substantially inhibiting entry of moisture from ambiant air. In some embodiments, the sealed multiwell plate is stored in a pouch containing desiccant. Similarly, separate vessels can undergo lyophilization, and can undergo lyophilization in a nest. The small amount of moisture entry into a sealed multiwell plate can be prevented in such ways.

Optimal lyophilization conditions are product-dependent. In some embodiments, a lyophilization procedure can comprise a thermal treatment step, e.g., at a temperature of about −30° C. to about −10° C. The thermal treatment step can have a duration, of, e.g., 30 minutes to 6 hours. For example, a thermal treatment step can be about 2 hours at about −20° C. In some embodiments, lyophilization procedure can comprise a primary drying step, e.g., at a temperature of about −50° C. to about −10° C. The primary drying step can have a duration, e.g., of about 10 hours to about 75 hours. In some embodiments, lyophilization procedure can comprise a secondary drying step, e.g., at a temperature of about −10° C. to about 40° C. The primary drying step can have a duration, e.g., of about 1 hour to about 24 hours. During the lyophilization, a vacuum is applied such that the pressure in the lyophilization chamber is lower than atmospheric pressure, e.g., in the range of about 10 mTorr to about 250 mTorr.

Other drying methods include spray drying, fluidized bed drying, dehumidifiers, desiccation, and drying of a filter cake (see NP Cheremisinoff (2000) Handbook of Chemical Preocessing Equipment, butterworth Heinemann, Boston, MA). Dehumidifiers are available from Bry Air, Inc., Sunbury, Ohio, and DST Seibu Giken, Wyomissing, PA Rotary dryers, conical dryers, and shelf dryers are available (McGill AirPressure LLC, Columbus, Ohio). In one embodiment, a vacuum dryer removes moisture by exposing the materials to reduced pressure, where heat lost through vaporization is replaced by a heat from a heat source or reservoir such as a water bath in which a vessel containing the materials, as in, e.g., commercially available rotary dryers. Exemplary desiccants include silica gel desiccants, molecular sieve desiccants such as aluminosilicate and synthetic zeolite, and bentonite desiccants.

In some embodiments, reaction mixtures are dried in the same vessel as that in which they will be reconstituted for use.

A lyophilized or otherwise solid or dried composition has a low water content, for example, under 5% water by weight, under 4%, under 3%, under 2%, under 1.0%, under 0.5%, under 0.2%, under 0.1%, under 0.05%, under 0.02%, under 0.01% by weight, and so on. In some embodiments, the solid composition has a mass ranging from about 5 mg to about 20 g, about 200 mg to about 20 g, about 1 g to about 20 g, about 5 g to about 20 g, about 5 mg to about 1 g, about 5 mg to about 500 mg, about 5 mg to about 200 mg, about 5 mg to about 100 mg, about 5 mg to about 50 mg, about 5 mg to about 20 mg, about 5 mg to about 10 mg, about 10 mg to about 200 mg, about 20 mg to about 200 mg, about 50 mg to about 200 mg, or about 100 mg to about 200 mg.

Lyophilized or otherwise solid or dried compositions are subject to storage before use. The period of storage can include a period of time in which the dried compositions are stored at room temperature exposed to ambient air. Such a period can be up to 3 hours, or alternatively, for up to 1.0 h, up to 1.5 h, up to 2.0 h, up to 2.5 h, up to 3.5 h, up to 4.0 h, up to 5.0 h, up to 6.0 h, up to 8.0 h, or ranges of any of the times, such as from 90 min to 180 min. The absolute humidity during such storage can be at least 2.3 g water per cubic meter of air, or alternatively, greater than 1.8, 2.0, 2.2, 2.4, 2.6, 2.8, 3.0 grams of water per cubic meter of air, up to the absolute humidity corresponding to about 95% relative humidity under the storage conditions. Alternatively relative humidity can be e.g., about 40% to about 95% relative humidity, such as about 40%, about 50%, about 60%, about 70%, about 80%, about 90%, or about 95% relative humidity.

Storage can also include a longer period in which dried or solid compositions are sealed substantially preventing contact with ambient air outside the seal. This period of storage can be for a long time, for example, at least a week, at least a month, at least six months, at least a year or at least two years. A period from one month to two years is exemplary.

Ranges of storage temperatures, for long-term storage or for long or short-term stability studies include, e.g., 0-2° C., 0-4° C., 2-4° C., 2-6° C., 20° C., 25° C., 30° C., 40° C., 50° C., 60° C., as well as subzero temperatures such as −4 to −2° C., −6 to −2° C., −8 to −2° C., −10 to −2° C., −20° C., −40° C., −60° C., −80° C., under liquid nitrogen. Preferrably, storage is above freezing point and in the range of about 4-8° C. Accelerated degradation studies can be conducted at about 25° C., about 30° C., about 35° C., about 40° C., for a period of, for example, one hour, two hours, four hours, 24 hours, two days, four days, eight days, one month, three months, 100 days, and so on. Conditions for storage or, alternatively, for stability testing, can be those that fluctuate in temperature, such as those that fluctuate from above to below a freezing point.

In some embodiments, the solution comprises water. In some embodiments, the solution comprises at least 10%, 20%, 30%, 40%, 50%, 55%, 60%, 65%, 70%, 75%, 80%, 85%, 90%, 95%, 96%, 97%, 98%, 99%, 99.5%, 99.6%, 99.7%, 99.8%, or 99.9% water by weight. In some embodiments, the solution comprises at least 10%, 20%, 30%, 40%, 50%, 55%, 60%, 65%, 70%, 75%, 80%, 85%, 90%, 95%, 96%, 97%, 98%, 99%, 99.5%, 99.6%, 99.7%, 99.8%, or 99.9% water by volume.

In some embodiments, the solution comprises a polar organic solvent. In some embodiments, the solution comprises at least 10%, 20%, 30%, 40%, 50%, 55%, 60%, 65%, 70%, 75%, 80%, 85%, 90%, 95%, 96%, 97%, 98%, 99%, 99.5%, 99.6%, 99.7%, 99.8%, or 99.9% polar organic solvent by weight. In some embodiments, the solution comprises at least 10%, 20%, 30%, 40%, 50%, 55%, 60%, 65%, 70%, 75%, 80%, 85%, 90%, 95%, 96%, 97%, 98%, 99%, 99.5%, 99.6%, 99.7%, 99.8%, or 99.9% polar organic solvent by volume. In some embodiments, the polar organic solvent comprises ethanol. In some embodiments, the polar organic solvent comprises isopropanol. In some embodiments, the polar organic solvent comprises DMSO. In some embodiments, the polar organic solvent comprises glycerol.

In some embodiments, the solution comprises a non-polar organic solvent. In some embodiments, the solution comprises at least 10%, 20%, 30%, 40%, 50%, 55%, 60%, 65%, 70%, 75%, 80%, 85%, 90%, 95%, 96%, 97%, 98%, 99%, 99.5%, 99.6%, 99.7%, 99.8%, or 99.9% non-polar organic solvent by weight. In some embodiments, the solution comprises at least 10%, 20%, 30%, 40%, 50%, 55%, 60%, 65%, 70%, 75%, 80%, 85%, 90%, 95%, 96%, 97%, 98%, 99%, 99.5%, 99.6%, 99.7%, 99.8%, or 99.9% non-polar organic solvent by volume.

In some embodiments, the total amount of solute in the solution is about 0.01% to about 50% (w/v), about 0.05% to about 50% (w/v), about 0.1% to about 50% (w/v), about 0.2% to about 50% (w/v), about 0.5% to about 50% (w/v), about 1% to about 50% (w/v), about 2% to about 50% (w/v), about 5% to about 50% (w/v), about 10% to about 50% (w/v), about 0.01% to about 25% (w/v), about 0.01% to about 10% (w/v), about 0.01% to about 5% (w/v), about 0.01% to about 2% (w/v), about 0.01% to about 1% (w/v), about 0.01% to about 0.1% (w/v), about 0.1% to about 1% (w/v), about 1% to about 2% (w/v), about 2% to about 5% (w/v), about 5% to about 10% (w/v), about 10% to about 20% (w/v), or about 20% to about 50% (w/v). In some embodiments, the total amount of solute in the solution is about 0.01% to about 50% (w/w), about 0.05% to about 50% (w/w), about 0.1% to about 50% (w/w), about 0.2% to about 50% (w/w), about 0.5% to about 50% (w/w), about 1% to about 50% (w/w), about 2% to about 50% (w/w), about 5% to about 50% (w/w), about 10% to about 50% (w/w), about 0.01% to about 25% (w/w), about 0.01% to about 10% (w/w), about 0.01% to about 5% (w/w), about 0.01% to about 2% (w/w), about 0.01% to about 1% (w/w), about 0.01% to about 0.1% (w/w), about 0.1% to about 1% (w/w), about 1% to about 2% (w/w), about 2% to about 5% (w/w), about 5% to about 10% (w/w), about 10% to about 20% (w/w), or about 20% to about 50% (w/w). In some embodiments, the total amount of solute in the solution is about 0.01% to about 50% (v/v), about 0.05% to about 50% (v/v), about 0.1% to about 50% (v/v), about 0.2% to about 50% (v/v), about 0.5% to about 50% (v/v), about 1% to about 50% (v/v), about 2% to about 50% (v/v), about 5% to about 50% (v/v), about 10% to about 50% (v/v), about 0.01% to about 25% (v/v), about 0.01% to about 10% (v/v), about 0.01% to about 5% (v/v), about 0.01% to about 2% (v/v), about 0.01% to about 1% (v/v), about 0.01% to about 0.1% (v/v), about 0.1% to about 1% (v/v), about 1% to about 2% (v/v), about 2% to about 5% (v/v), about 5% to about 10% (v/v), about 10% to about 20% (v/v), or about 20% to about 50% (v/v).

Exemplary volumes of a solution include about 1 ul, about 5 ul, about 10 ul, about 20 ul, about 24 ul, about 50 ul, about 100 ul, about 200 ul, about 300 ul, about 400 ul, about 500 ul about 600 ul, about 700 ul, about 800 ul, about 900 ul, about 1,000 µl (1 mL), about 2 mL, about 5 mL, about 10 mL, about 20 mL, about 50 mL, and so on. Reconstituted compositions can be formed at the same volume, a lower volume, or greater volume than the solution before drying. A lower volume can be about 90%, about 80%, about 60%, about 40%, about 20%, about 10%, or about 5%, relative to the bulk reagents. A greater volume can be about 120%, 140%, 160%, 180%, 200% (2-fold), about 4-fold, about 6-fold, about 8-fold, about 10-fold, about 20-fold, that of the bulk reagents.

In some embodiments, the solution comprises a bulking agent. In some embodiments, the solution comprises one or more enzymes. In some embodiments, the solution comprises at least one oligonucleotide useful for performing a molecular assay. In some embodiments, the solution comprises a buffer. In some embodiments, the solution comprises a salt. In some embodiments, the solution comprises one or more nucleoside triphosphates. In some embodiments, the solution comprises one or more deoxynucleoside triphosphates. In some embodiments, the solution comprises dATP, dGTP, dCTP, and at least one of dTTP and dUTP.

In some embodiments, the solution is free of inorganic salt. In some embodiments, the solution contains from about 5 mM to 0 mM inorganic salt. Additional exemplary concentration ranges of inorganic salt in a solution are from about 4 mM to 0 mM, about 3 mM to 0 mM, about 2 mM to 0 mM, about 1 mM to 0 mM, or about 500 uM to 0 mM. Additional common inorganic salts for amplification and detection reaction mixtures include one or more of sodium, potassium, manganese, magnesium and chloride, to name a few.

In some embodiments, the solution comprises 5 mM or less of inorganic salt, and: the inorganic salts are present in a mass per microliter of 0.373 µg/µl or less, or 0.332 µg/µl or less, or 0.292 µg/µl or less; sodium chloride is present at a mass per microliter of 0.292 µg/µl or less, of 0.146 µg/µl or less, or of 0.0 µg/µl; sodium is present at a mass per microliter of 0.115 µg/µl or less, of 0.057 µg/µl or less, or of 0.0 ug/µl; potassium chloride is present at a mass per microliter of 0.373 µg/µl or less, of 0.186 µg/µl or less, or of 0.0 ug/µl; potassium is present at a mass per microliter of 0.196 µg/µl or less, of 0.098 µg/µl or less, or of 0.0 ug/µl; or chloride is present at a mass per microliter of 0.355 µg/µl or less, of 0.178 µg/µl or less, of 0.089 µg/µl or less, or of 0.0 ug/µl.

In some embodiments, the solution comprises 4 mM or less of inorganic salt, and: the inorganic salts can be present in a mass per microliter of 0.298 µg/µl or less, or 0.266 µg/µl or less, or 0.234 µg/µl or less; sodium chloride is present at a mass per microliter of 0.234 µg/µl or less, of 0.117 µg/µl or less, or of 0.0 ug/µl; sodium is present at a mass per microliter of 0.092/µlµg/µl or less, of 0.046 µg/µl or less, or of 0.0 ug/µl; potassium chloride is present at a mass per microliter of 0.298 µg/µl or less, of 0.149 µg/µl or less, or of 0.0 ug/µl; potassium is present at a mass per microliter of 0.156 µg/µl or less, of 0.078 µg/µl or less, or of 0.0 ug/µl; or chloride is present at a mass per microliter of 0.284 µg/µl or less, of 0.142 µg/µl or less, of 0.071 µg/µl or less, or of 0.0 ug/µl.

In some embodiments, the solution comprises 3 mM or less of inorganic salt, and: the inorganic salts are present in a mass per microliter of 0.224 µg/µl or less, or 0.199 µg/µl or less, or 0.175 µg/µl or less; sodium chloride is present at a mass per microliter of 0.175 µg/µl or less, of 0.088 µg/µl or less, or of 0.0 µg/µl; sodium is present at a mass per microliter of 0.069 µg/µl or less, of 0.034 µg/µl or less, or of 0.0 µg/µl; potassium chloride is present at a mass per microliter of 0.224 µg/µl or less, of 0.112 µg/µl or less, or of 0.0 µg/µl; potassium is present at a mass per microliter of 0.117 µg/µl or less, of 0.059 µg/µl or less, or of 0.0 µg/µl; or chloride is present at a mass per microliter of 0.213 µg/µl or less, of 0.107 µg/µl or less, of 0.053 µg/µl or less, or of 0.0 µg/µl.

In some embodiments, the solution comprises 2 mM or less of inorganic salt, and: the inorganic salts are present in a mass per microliter of 0.149 µg/µl or less, or 0.133 µg/µl or less, or 0.117 µg/µl or less; sodium chloride is present at a mass per microliter of 0.117 µg/µl or less, of 0.058 µg/µl or less, or of 0.0 µg/µl; sodium is present at a mass per microliter of 0.046 µg/µl or less, of 0.023 µg/µl or less, or of 0.0 µg/µl; potassium chloride is present at a mass per microliter of 0.149 µg/µl or less, of 0.075 µg/µl or less, or of 0.0 µg/µl; potassium is present at a mass per microliter of 0.078 µg/µl or less, of 0.039 µg/µl or less, or of 0.0 µg/µl; or chloride is present at a mass per microliter of 0.142 µg/µl or less, of 0.071 µg/µl or less, of 0.036 µg/µl or less, or of 0.0 µg/µl.

In some embodiments, the solution comprises 1 mM or less of inorganic salt, and: the inorganic salts are present in a mass per microliter of 0.075 µg/µl or less, or 0.066 µg/µl or less, or 0.058 µg/µl or less; sodium chloride is present at a mass per microliter of 0.058 µg/µl or less, of 0.029 µg/µl or less, or of 0.0 µg/µl; sodium is present at a mass per microliter of 0.023 µg/µl or less, of 0.011 µg/µl or less, or of 0.0 µg/µl; potassium chloride is present at a mass per microliter of 0.075 µg/µl or less, of 0.037 µg/µl or less, or of 0.0 µg/µl; potassium is present at a mass per microliter of 0.039 µg/µl or less, of 0.020 µg/µl or less, or of 0.0 µg/µl; or chloride is present at a mass per microliter of 0.071 µg/µl or less, of 0.036 µg/µl or less, of 0.018 µg/µl or less, or of 0.0 µg/µl.

In some embodiments, the solution comprises 500 uM or less of inorganic salt, and: the inorganic salts are present in a mass per microliter of 0.037 µg/µl or less, or 0.033 µg/µl or less, or 0.029 µg/µl or less; sodium chloride is present at a mass per microliter of 0.029 µg/µl or less, of 0.015 µg/µl or less, or of 0.0 µg/µl; sodium is present at a mass per microliter of 0.011 µg/µl or less, of 0.006 µg/µl or less, or of 0.0 µg/µl; potassium chloride is present at a mass per microliter of 0.037 µg/µl or less, of 0.019 µg/µl or less, or of 0.0 µg/µl; potassium is present at a mass per microliter of 0.020 µg/µl or less, of 0.010 µg/µl or less, or of 0.0 µg/µl; or chloride is present at a mass per microliter of 0.036 µg/µl or less, of 0.018 µg/µl or less, of 0.009 µg/µl or less, or of 0.0 µg/µl.

In some embodiments, the solution comprises from about 5 mM to about 500 uM of inorganic salt, and: inorganic salts are present in a mass per microliter from about 0.373 µg/µl to about 0.029 µg/µl; sodium chloride is present at a mass per microliter 0.292 µg/µl to about 0.029 µg/µl; sodium is present at a mass per microliter 0.115 µg/µl to about 0.006 µg/µl; potassium chloride is present at a mass per microliter from about 0.373 µg/µl to about 0.019 µg/µl; potassium is present at a mass per microliter 0.196 µg/µl to about 0.010 µg/µl; chloride is present at a mass per microliter of 0.355 µg/µl to about 0.009 µg/µl; the inorganic salts are present in a mass per microliter from about 0.373 µg/µl to about 0.029 µg/µl, and the sodium chloride can be present at a mass per microliter of about 0 µg/µl; or inorganic salts are present in a mass per microliter from about 0.373 µg/µl to about 0.029 µg/µl, and the potassium chloride is present at a mass per microliter of about 0 µg/µl.

In some embodiments, at least one of one or more nucleoside triphosphates is present in an amount ranging from about 0.1 mM to about 0.3 mM or from about 0.2 mM to about 0.6 mM in the solution.

In some embodiments, the solution comprises a pharmaceutically active agent, e.g., one or more single unit doses of a pharmaceutically active agent. In some embodiments, the solution further comprises a pharmaceutically acceptable salt.

In some embodiments, the solution comprises reagents sufficient for performing a nucleic acid synthesis or amplification assay. "Reagents sufficient for performing a nucleic acid synthesis or amplification assay" mean a set of reagents, other than a solvent and a sample or template nucleic acid, that can be used to perform nucleic acid synthesis, such as a polymerase, an appropriate divalent cation salt, and nucleotide triphosphates. Such reagent sets can be customized for different types of amplification including PCR, RT-PCR and transcription mediated amplification by the choice of enzyme and other components.

In some embodiments, the solution comprises a capture probe or a hydrolysis probe. In some embodiments, the solution comprises an RNase inhibitor. In some embodiments, the RNase inhibitor is present in the solution at a concentration from about 0.12 U/ul to about 0.20 U/ul. In some embodiments, the solution comprises a chelating agent. In some embodiments, the chelating agent is present in the solution at a concentration from 1.5 mM to 2.0 mM. In some embodiments, the solution comprises a detergent.

In some embodiments, solutions (sometimes referred to as prelyophilized mixtures) according to the disclosure comprise one, two, three, or all of a polymerase; nucleotides for use in amplification and detection reactions; an organic buffer, e.g., Tris; and a bulking agent such as trehalose or raffinose or a combination thereof. Solutions may or may not also include one or more nucleic acids. Solutions may additionally include reverse transcriptase enzymes, chelators, and RNase inhibitors.

Nucleotides for incorporation into an amplification reaction are typically provided as dNTPs. Exemplary concentrations for dNTPs are 0.1 to 0.3 mM of dATP; 0.1 to 0.3 mM of dGTP; 0.1 to 0.3 mM of dCTP; 0.2 to 0.6 mM of dTTP; 0.2 to 0.6 mM of dUTP; and preferably about 0.2 mM of dATP; about 0.2 mM of dGTP; about 0.2 mM of dCTP and 0.4 mM dTTP or dUTP.

An exemplary solution has 0.1-0.3 mM and more preferably 0.2 mM dATP, dGTP and dCTP, as well as 0.2-0.6 mM and more preferrably 0.4 mM, dUTP or dTTP, and 0.3-0.8 U/µL polymerase. In some compositions, the polymerase is a hot start Taq polymerase. In some compositions, the polymerase is a GoTaq®MDx Hot Start polymerase. Some compositions also include RNAasin™ RNAase inhibitor at 0.12-0.20 U/µL. Some compositions also include EDTA, optionally at 1.5-2.0 mM. Such a composition also includes trehalose at 0.16-0.32 M, EDTA at 1.5-2.0 mM and the polymerase is Taq at 0.3-0.45 U/µL.

The present disclosure provides reagents for PCR reactions, including real-time PCR reactions. (Real-time PCR Handbook, Life Technologies (2014); Kutyavin et al (2000) Nucleic Acids Res. 28:655; Afonina et al (2002) Biotechniques. 32:940). In real-time PCR, magnesium salt is typically used at a final concentration of about 3-6 mM (Realtime PCR Handbook, supra). In some embodiments, the disclosure provides reagents for multiplex PCR reactions, that is, where a plurality of primer pairs is provided for the amplification and detection of a plurality of targets. The disclosure provides primers and probes for PCR reactions. Primers and/or probes comprise target hybridizing sequences, and can further comprise one or more of non-target hybridizing sequences, nucleotide analogs, detectable moieties, and non-nucleotide linkers (see e.g., WO 2010/151566 and WO 2013/126793). In some embodiments, one or more primers or probes are suitable for hybridization or do hybridize to a target, template, or sample nucleic acid under stringent conditions. Thermocyclers are available (Applied Biosystems ProFlex® PCR System and Veriti® Thermal Cycler). Gel scanners for quantifying PCR products are available (Agilent® 2100 Bioanalyzer®, Bio-Rad® densitometer).

After formation of a solution it may be left at room temperature for a significant period before drying. The period can be for up to 8 hr before drying step is initiated, or alternatively, for up to 1 hr, up to 2 hr, up to 4 hr, up to 6 hr, up to 10 hr, up to 12 hr, or up to 14 hr before the drying step is initiated. Inclusion of a substantial amount of salts in the solution together with other reagents, e.g., PCR reagents, can result in undesired hybridization products and other by-products during this incubation period. Such undesired hybridization and by-products can be reduced or eliminated by forming the solution essentially without inorganic salt, e.g., less than about 5 mM inorganic salt.

The presence of inorganic salts in a solution can result in one or more of the following undesirable properties depending on the other components of the solution. Nucleic acids may hybridize together, the hybridization being stimulated by the presence of inorganic ions from the salt such as potassium, sodium, manganese, magnesium and/or chloride. Also in the presence of inorganic divalent cations like manganese and magnesium, undesirable enzyme activity can occur, such as polymerase processivity. Such undesired activity can occur with non-hot-start enzymes and with hot-start enzymes. As a result of nucleic acid hybridization and enzyme activity in the presence of salt, undesired side-products may start to form. Additionally, inorganic salts are hygroscopic and can draw atmospheric moisture into a solid composition. Rehydration of the solid composition can reduce storage stability, enzyme stability, and allow for additional spurious side product formation.

In some embodiments, the solid composition is formed by drying a solution according to the disclosure. Thus, the solid composition according to the disclosure can contain any of the solutes that a solution according to the disclosure can contain. For example, in some embodiments, the solid composition comprises a bulking agent. In some embodiments, the solid composition comprises one or more enzymes. In some embodiments, the solid composition comprises at least one oligonucleotide useful for performing a molecular assay. In some embodiments, the solid composition comprises a buffer. In some embodiments, the solid composition comprises a salt. In some embodiments, the solid composition is free of inorganic salt. In some embodiments, the solid composition comprises one or more nucleoside triphosphates. In some embodiments, the solid composition comprises one or more deoxynucleoside triphosphates. In some embodiments, the solid composition comprises dATP, dGTP, dCTP, and at least one of dTTP and dUTP. In some embodiments, the solid composition comprises a capture probe or a hydrolysis probe. In some embodiments, the solid composition comprises an RNase inhibitor. In some embodiments, the solid composition comprises a chelating agent. In some embodiments, the solid composition comprises a detergent.

In some embodiments, the solid composition comprises reagents sufficient for performing a nucleic acid synthesis or amplification assay. In some embodiments, the solid composition comprises one, two, three, or all of a polymerase; nucleotides for use in amplification and detection reactions; an organic buffer, e.g., Tris; and a bulking agent such as trehalose or raffinose or a combination thereof. Solutions may or may not also include one or more nucleic acids. Solutions may additionally include reverse transcriptase enzymes, chelators, and RNase inhibitors.

A solid composition can contain reagents to provide one single unit dose (SUD), or optionally, two or more SUDs. A single unit dose is a collection of reagents necessary to perform an amplification and/or a detection reaction on no more than a single sample. Single unit dose can refer to a liquid reagent or a dried pellet. It is notable that a single unit dose, as referred to herein, need not contain all of the reagents nesessary to perform an amplification and/or detection reaction on a single sample. A single unit dose may lack a reagent needed for performing amplification and/or detection reactions. Similarly, a single unit dose may contain an insufficient amount of a reagent for performing amplification and/or detection reactions. By way of example only, a dried single unit dose pellet may comprise adequate units of Taq polymerase for performing an amplification reaction, but may contain no magnesium. In an example such as this, the magnesium can be added to the dried single unit dose pellet, such as by way of a reconstitution liquid. Also by way of example only, a dried single unit dose may comprise an inadequate amount of dNTPs for performing an amplification reaction. In an example such as this, the remainder of the dNTPs can be added to the dried single unit dose pellet, such as by way of a reconstitution liquid. Ordinarily skilled artisans in posssession of this disclosure will readily generate SUDs and dried pellet SUDs with varied compositions, as these examples are non limiting. As used herein, the phrase "contains a single unit dose" and other grammatical forms thereof are not open to unlimited amounts, i.e., a solution, composition, or concavity (e.g., well) that contains a single unit dose does not contain two or more SUDs.

In some embodiments, the solid composition comprises a pharmaceutically active agent, e.g., one or more single unit doses of a pharmaceutically active agent. In some embodiments, the solid composition further comprises a pharmaceutically acceptable salt.

In some embodiments, a solid composition is made from drying a solution comprising 5 mM or less of an inorganic salt, and the percent mass of the inorganic salt to the mass of the solid composition is 0.311% or less, 0.277% or less, or 0.244% or less. For example, the solution can comprise 4 mM or less of an inorganic salt, and the percent mass of the inorganic salt to the mass of the solid composition is 0.249% or less, 0.222% or less, or 0.195% or less. The solution can comprise 3 mM or less of an inorganic salt, and the percent mass of the inorganic salt to the mass of the solid composition is 0.186% or less, 0.166% or less, or 0.146% or less. The solution can comprise 2 mM or less of an inorganic salt, and the percent mass of the inorganic salt to the mass of the solid composition is 0.124% or less, 0.111% or less, or 0.097% or less. The solution can comprise 1 mM or less of an inorganic salt, and the percent mass of the inorganic salt to the mass of the solid composition is 0.062% or less, 0.055% or less, or 0.049% or less. The solution can comprise 500 uM or less of an inorganic salt, and the percent mass of the inorganic salt to the mass of the solid composition is 0.031% or less, 0.028% or less, or 0.024% or less. The solution can comprise from 5 mM to 500 uM of an inorganic salt, and the percent mass of the inorganic salt to the mass of the solid composition is from about 0.311% to 0.024%. In some embodiments, the percent mass of the sodium chloride to mass of the solid composition is about 0%, or the percent mass of the potassium chloride to mass of the solid composition is about 0%. Also provided is a vessel that contains a dried single unit dose of one of the foregoing solid compositions. Also provided is a multiwell plate comprising two or more wells, wherein at least two, three, four five, six, ten, twelve, or all of the wells contain a dried single unit dose of one of the foregoing solid compositions.

In some embodiments, a reconstitution liquid is used or provided. For example, the reconstitution liquid can be added to a solid composition, e.g., on a plasma-treated surface. In some embodiments, a reconstitution liquid is provided in a kit.

In some embodiments, the reconstitution liquid comprises water. In some embodiments, the reconstitution liquid comprises at least 10%, 20%, 30%, 40%, 50%, 55%, 60%, 65%, 70%, 75%, 80%, 85%, 90%, 95%, 96%, 97%, 98%, 99%, 99.5%, 99.6%, 99.7%, 99.8%, or 99.9% water by weight. In some embodiments, the reconstitution liquid comprises at least 10%, 20%, 30%, 40%, 50%, 55%, 60%, 65%, 70%, 75%, 80%, 85%, 90%, 95%, 96%, 97%, 98%, 99%, 99.5%, 99.6%, 99.7%, 99.8%, or 99.9% water by volume.

In some embodiments, the reconstitution liquid comprises a polar organic solvent. In some embodiments, the reconstitution liquid comprises at least 10%, 20%, 30%, 40%, 50%, 55%, 60%, 65%, 70%, 75%, 80%, 85%, 90%, 95%, 96%, 97%, 98%, 99%, 99.5%, 99.6%, 99.7%, 99.8%, or 99.9% polar organic solvent by weight. In some embodiments, the reconstitution liquid comprises at least 10%, 20%, 30%, 40%, 50%, 55%, 60%, 65%, 70%, 75%, 80%, 85%, 90%, 95%, 96%, 97%, 98%, 99%, 99.5%, 99.6%, 99.7%, 99.8%, or 99.9% polar organic solvent by volume. In some embodiments, the polar organic solvent comprises ethanol. In some embodiments, the polar organic solvent comprises isopropanol. In some embodiments, the polar organic solvent comprises DMSO. In some embodiments, the polar organic solvent comprises glycerol.

In some embodiments, the reconstitution liquid comprises a non-polar organic solvent. In some embodiments, the reconstitution liquid comprises at least 10%, 20%, 30%, 40%, 50%, 55%, 60%, 65%, 70%, 75%, 80%, 85%, 90%, 95%, 96%, 97%, 98%, 99%, 99.5%, 99.6%, 99.7%, 99.8%, or 99.9% non-polar organic solvent by weight. In some embodiments, the reconstitution liquid comprises at least 10%, 20%, 30%, 40%, 50%, 55%, 60%, 65%, 70%, 75%, 80%, 85%, 90%, 95%, 96%, 97%, 98%, 99%, 99.5%, 99.6%, 99.7%, 99.8%, or 99.9% non-polar organic solvent by volume.

In some embodiments, the reconstitution liquid comprises a bulking agent. In some embodiments, the reconstitution liquid comprises one or more enzymes. In some embodiments, the reconstitution liquid comprises at least one oligonucleotide useful for performing a molecular assay. In some embodiments, the reconstitution liquid comprises a buffer. In some embodiments, the reconstitution liquid comprises a salt. In some embodiments, the reconstitution liquid is free of inorganic salt. In some embodiments, the reconstitution liquid comprises one or more nucleoside triphosphates. In some embodiments, the reconstitution liquid comprises one or more deoxynucleoside triphosphates. In some embodiments, the reconstitution liquid comprises dATP, dGTP, dCTP, and at least one of dTTP and dUTP.

In some embodiments, the reconstitution liquid comprises reagents sufficient for performing a nucleic acid synthesis or amplification assay.

In some embodiments, the reconstitution liquid comprises a capture probe or a hydrolysis probe. In some embodiments, the reconstitution liquid comprises an RNase inhibitor. In some embodiments, the reconstitution liquid comprises a chelating agent. In some embodiments, the reconstitution liquid comprises a detergent.

In some embodiments, the reconstitution liquid does not contain or is substantially free of organic solutes. In some embodiments, the reconstitution liquid does not contain or is substantially free of organic solutes having a molecular mass greater than about 1 kDa. In some embodiments, the reconstitution liquid does not contain or is substantially free of organic solutes having a molecular mass greater than about 10 kDa. "Substantially free" means that the referenced substance, if present at all, is at a sufficiently low level so as not to affect the suitability of the composition in which it occurs for an appropriate purpose, e.g., reconstitution, detection, amplification, or the like.

In some embodiments, the reconstitution liquid provides 3.8-4.4 mM $MgCl_2$, and 50-80 mM KCl in water. The reconstitution liquid can also contain 0.012-0.020% methyl paraben, 0.006-0.010% propyl paraben, and/or 0.26% absolute ethanol among other components.

In some embodiments, the reconstitution liquid comprises a pharmaceutically acceptable salt. In some embodiments, the reconstitution liquid and the solid composition (e.g. a solid composition comprising a pharmaceutically active agent) are combined to provide a pharmaceutically acceptable composition, e.g., comprising a single unit dose of a pharmaceutically active agent.

Reconstitution time can be under 1 sec, under 2 sec, under 5 sec, under 10 sec, under 15 sec, under 20 sec, under 50 sec, or under 60 sec (1 minute), after aqueous solution suitable for intended use of the solid composition is contacted with the the solid composition, with contact optionally facilitated by any of shaking, tapping vortexing, rocking, drawing in and out of a pipet tip, or folding or squeezing of a malleable vial. An exemplary reconstitutition time is 2-10 sec. Reconstitution time can be measured with the reconstitution liquid at any of refrigerator temperature (about 4° C.), ambient temperature solution about 23° C., or with a warm solution at about 37° C. Typically, the dried composition has been removed from a refrigerator and is cold before addition of the reconstitution liquid. The environment (the room) for any of these procedures is typically ambient temperature or about 21° C.-25° C., e.g., 23° C. The time at which a substance is determined to be reconstituted can be, for example, the time at which the substance is determined to be completely solubilized. Complete solubilization can be determined by visual inspection, for example, where absence of turbidity or absence of a schlieren pattern is a measure of complete solubilization. Alternatively, complete solubilization can be determined by way of an optical instrument, such as a machine that measures light scattering.

Optional additional components (e.g., in a solution, solid composition, or reconstitution liquid) include without limitation any of PCR reagents, surfactants, primers, probes, template, methyl paraben, and propyl paraben. An exemplary concentration for methyl paraben is 0.01-0.024% by weight, for example about 0.016%, or alternatively, about 0.010%, about 0.014%, about 0.016%, about 0.020%, about 0.024%, or any range bordered by these values. An exemplary concentration range of propyl paraben is 0.002-0.016% or 0.008%, or alternatively, about 0.002%, about 0.004%, about 0.006%, about 0.008%, about 0.010%, about 0.012%, about 0.014%, about 0.016% or any range bordered by these values.

In some embodiments, the bulking agent (e.g., present in a solution or solid composition) comprises a saccharide. Exemplary bulking agents are trehalose or raffinose or a combination thereof. Other bulking agents that can be used include sucrose, mannitol, trehalose plus mannitol, sucrose plus mannitol, sucrose plus glycine, and hydroxyethyl starch. See, Cleland et al (2001) J. Pharm. Sci. 90:310; Meyer et al (2009) Eur. J. Pharm. Sci. 38:29; Webb et al (2003) J. Pharm. Sci. 92:715; Garzon Rodrigues et al (2004) J. Pharm. Sci. 93:684; Qiu et al (2012) Int. J. Pharmaceuticals. 437:51); Van Dijk-Wolthuis et al (1997) Polymer. 38:6235 6242. Hydroxyethyl starch is classified as, hetastarch, hexastarch, pentastarch, and tetrastarch (see, e.g., WO2014/099198 of Chow). The bulking agent is preferably present at a concentration of 0.16 M to 0.32 M, or alternatively, at 0.04 to 0.12M, 0.08 to 0.16M, 0.12 to 0.20M, 0.16 to 0.24M, 0.20 to 0.28M, 0.24 to 0.32M, 0.28 to 0.36M, 0.32 to 0.40M, or any combination of said ranges, such as 0.08 to 0.24M. In some embodiments, the bulking agent comprises at least one of sucrose, mannitol, glycine, hydroxyethyl starch, raffinose, or trehalose. In some embodiments, the bulking agent comprises trehalose.

In some embodiments, one or more enzymes (e.g., present in a solution, solid composition, or reconstitution liquid) include at least one of a DNA polymerase, an RNA polymerase, a ligase, a kinase, a phosphatase, a protease, an exonuclease, and an endonuclease. In some embodiments, the one or more enzymes include a thermostable DNA polymerase. In some embodiments, the thermostable DNA polymerase is a hot-start thermostable DNA polymerase or is complexed with an antibody. In some embodiments, the one or more enzymes include a DNA-dependent polymerase, reverse transcriptase or other enzyme that is present in the solution at a concentration from about 0.20 U/ul to about 0.72 U/ul or from about 0.1 U/ul to about 0.6 U/ul.

DNA polymerase enzymes are commercially available or can be prepared by a user. One example of a polymerase enzyme is a Taq polymerase commercially available from Qiagen (Germantown, MD, cat #201203). Another example of a Taq polymerase is commercially available as GoTaq® G2 Flexi DNA polymerase (Promega, Madison, WI, cat

M7801). Other DNA polymerases that are commercially available include, but are not limited to, Tth DNA polymerase (e.g., Sigma-Aldrich, St. Louis, MO, cat #11480022001), and chimeric DNA polymerases such as Phusion® High-Fidelity DNA Polymerase (NEB, Ipswich, MA, cat #M05305). Also commercially available are hot-start DNA polymerase enzymes. For example, a Taq polymerase is commercially available as GoTaq® Hot Start Polymerase (Promega, cat #M5001). The GoTaq® Hot Start polymerase is an antibody mediated hot start enzyme, where the Taq polymerase is bound to an antibody that blocks polymerase activity. The blocking antibody is denatured using high heat, thus during the initial heat step of a PCR reaction, the antibody is denatured and polymerase activity is restored. Various antibodies can be used with hot start method, for example, TAQSTART antibody (Clontech Laboratories, Mountain View, CA, cat #R028A). Similarly, other hot start polymerase enzymes are available, including chemically-mediated hot start polymerases. Equivalent polymerase and antibodies are available from a variety of commercial sources and, alternatively, can be prepared by the user.

Reverse transcriptase enzymes are commercially available or can be prepared by a user. Examples of commercially available reverse transcriptase include, but are not limited to, MMLV (Maloney Murine Leukemia Virus) reverse transcriptase & SuperScript® III Reverse Transcriptase (e.g., ThermoFisher Scientific, Carlsbad, CA, cat #s 28025-013 & 18080-044), MMLV RT (Sigma-Aldrich, cat #M1302), AMV Reverse Transcriptase (NEB, Ipswich, MA, cat #M0277S), and GoScript™ reverse transcriptase (Promega, cat #A50003). GoScript reverse transcriptase includes a reverse transcriptase and a set of reagents for synthesis of first-strand cDNA optimized for quantitative PCR amplification. Equivalent reverse transcriptase and reagents are available from various commercial sources and, alternatively, can be prepared by the user.

Exemplary concentrations for DNA polymerase enzyme in single unit doses are 0.01-1.0 U/ul. For example 0.32 U/ul, or 0.4 U/ul or 0.72 U/ul, or 0.32-0.4 U/ul, or 0.4-0.72 U/ul, or 0.05-0.3 U/ul, or 0.8-1.0 U/ul. One unit of DNA polymerase is defined as the amount of enzyme required to catalyze the incorporation of 10 nanomoles of dNTPs into acid-insoluble material in 30 minutes at 74° C. Exemplary concentrations of reverse transcriptase enzyme in single unit doses are 0.01 U/ul-1.0 U/ul. One unit of reverse transcriptase is defined as the amount of enzyme required to catalyze the transfer of 1 nmol of deoxynucleotide into acid-precipitable material in 10 minutes at 37° C.

In some embodiments, the oligonucleotide(s) (e.g., present in a solution, solid composition, or reconstitution liquid) are one or more amplification oligomers (e.g., primers, promoter-primer), capture probes, detection probes Taqman probes, positive control template, and negative control template. In some embodiments, at least one of the oligonucleotides comprises a label. In some embodiments, the label is a fluorescent, chemiluminescent, affinity, or radioactive label. In some embodiments, the label is not a nucleotide, not a phosphate, not a carbohydrate, or not a nucleobase.

In some embodiments, reagents sufficient for performing a nucleic acid synthesis or amplification assay (e.g., present in a solution, solid composition, or reconstitution liquid) further comprise a primer, a promoter-primer, or a primer pair (optionally including a promoter-primer). In some embodiments, reagents sufficient for performing a nucleic acid synthesis or amplification assay further comprise one or more of a buffer, stabilizer, preservative, or other auxiliary substances.

In some embodiments, the buffer (e.g., present in a solution, solid composition, or reconstitution liquid) is an organic buffer. In some embodiments, the buffer is an inorganic buffer.

An exemplary organic buffer is Tris. Alternative organic buffers that can be incorporated into solutions, solid compositions, or reconstitution liquids of the disclosure include phosphate, citrate, acetate, CHES, histidine, and Good's buffers, such as HEPES, MES, MOPS, tricine, and glycinamide, as well as buffer combinations. Other organic buffers include succinate, citrate, gluconate, phosphate, and the like. In some embodiments, buffers are effective in a pH range from about 5.5 to about 7.0 or about 6.0 to about 7.5, e.g., a pH of about 6.5. Examples of buffers that control the pH in this range include succinate (such as sodium succinate), gluconate, histidine, citrate and other organic acid buffers.

In some embodiments, the chelating agent (e.g., present in a solution, solid composition, or reconstitution liquid) is one or more of EDTA (ethylenediaminetetraacetic acid), EGTA (ethylene glycol tetraacetic acid), EDDS (ethylenediamine-N,N'-disuccinic acid), MGDA (methylglycindiacetic acid), or DTPA (diethylene triamine pentaacetic acid). Exemplary concentrations for chelating agents are from about 1 mM to 2.5 mM.

In some embodiments, the detergent (e.g., present in a solution, solid composition, or reconstitution liquid) is a nonionic, cationic, anionic, or zwitterionic detergent. Detergents include ionic (cationic or anionic), non-ionic and zwitterionic detergents available from a number of commercial vendors (e.g., Geno Technology, Inc., St. Louis, MO). Examples include, but are not limited to, lithium lauryl sulfate, amprolium hydrochloride, benzalkonium chloride, choline p-toluenesulfonate salt, dodecyltrimethylammonium chloride, 3-[(3-Cholamidopropyl)dimethylammonio]-1-propanesulfonate, ethylhexadecyldimethylammonium bromide, hexadecylpyridinium chloride, hexadecyltrimethylammonium chloride, sodium dodecyl sulfate, hexadecyltrimethylammonium p-toluenesulfonate, Luviquat™, methylbenzethonium chloride, myristyltrimethylammonium bromide, N,N',N'-Polyoxyethylene (10)-N-tallow-1,3-diaminopropane liquid, oxyphenonium bromide, tetraheptylammonium bromide, tetrakis(decyl)ammonium bromide, tricaprylylmethylammonium chloride, Amidosulfobetaine-16, tridodecylmethylammonium chloride, trimethyloctadecylammonium bromideNonidet P-40®, Tween-20®, Tween-80®, Brij-35®, Triton X-100®.

RNase inhibitor proteins include native and recombinant 50 kDa proteins that inhibit RNase A family and human placental RNases by noncovalently binding to RNases in a 1:1 ratio (Promega Corp., Madison, WI). See, Botella-Estrada et al (2001) Cancer Gene Ther. 8:278; Polakowski et al (1992) EXS. 61:428. Exemplary concentrations of RNase inhibitor about 0.04 U/ul to about 0.4 U/ul. One unit is defined as the amount of RNasin® Ribonuclease Inhibitor required to inhibit the activity of 5 ng of ribonuclease A by 50%. Activity is measured by the inhibition of hydrolysis of cytidine 2',3'-cyclic monophosphate by ribonuclease A.

In some embodiments, before the drying step, the solution is dispensed onto the surface. In some embodiments, before the dispensing step, a surface is plasma-treated to form the plasma-treated surface.

In some embodiments, the solid composition is within a concavity of the plasma-treated surface. In some embodiments, the solid composition is within a vessel comprising the plasma-treated surface. In some embodiments, the vessel comprises a tube. In some embodiments, the vessel is a multiwell plate comprising a plurality of wells. In some embodiments, the volume of the vessel, tube, or well ranges from about 40 ul to about 60 ml. In some embodiments, after the drying step, the solid composition is sealed in a vessel comprising the plasma-treated surface.

As discussed above, certain embodiments involve multiwell plates comprising two or more wells. In some embodiments, the two or more wells comprise walls that are constructed from a material comprising a low moisture-vapor transmission rate, thermal conductivity, optical transparancy, low autofluorescence, or a combination thereof. In one aspect, a one or more wells comprise walls that are cone shaped. In some embodiments, the two or more wells comprise walls configured to fit into a PCR thermal-cycler for performing a PCR amplification reaction on a reaction mixture contained within the well. In some embodiments, the two or more wells comprise walls configured to fit into a thermally conductive tube receiving area of a device for performing PCR, TMA, or other nucleic acid amplification reactions. In some embodiments, the two or more wells comprise an opening for access to the chamber of the well. In some embodiments, the two or more wells each comprise a cap to seal the opening of the associated well. In some embodiments, an opening of each of the two or more wells is sealed with a cap that is a low moisture-vapor transmission rate foil. In some embodiments, an opening of each of the two or more wells is sealed with a cap that is a low moisture-vapor transmission rate elastomeric substance. In one aspect, a multiwell plate comprises two or more wells as described herein, wherein a chamber of each of the two or more wells contains a dried single unit dose composition comprising a polymerase enzyme and an inorganic salt, wherein the percent mass of the inorganic salt to the mass of the pellet is from about 0.311% to 0.024%. In one aspect, a multiwell plate comprises two or more wells as described herein, wherein a chamber of each of the two or more wells contains a dried single unit dose composition comprising a reverse transcriptase enzyme and an inorganic salt, wherein the percent mass of the inorganic salt to the mass of the pellet is from about 0.311% to 0.024%. In one aspect, a multiwell plate comprises two or more wells as described herein, and wherein a chamber of each of the two or more wells contains a dried single unit dose composition comprising a polymerase enzyme, a reverse transcriptase enzyme, and an inorganic salt, wherein the percent mass of the inorganic salt to the mass of the pellet is from about 0.311% to 0.024%.

Solid compositions provided here can be reconstituted with a reconstitution liquid as discussed above and then used in one or more further steps. A sample to be analyzed can be added to the solid composition either before reconstitution, at the same time as reconstitution, or after reconstitution. In some embodiments, the entire composition after reconstitution is used for combining with sample, and here the relative volumes of reconstitution liquid/sample can be, for example, about 9.9/0.1, 9.8/0.2, 9.5/0.5, 9/1, 8/2, 7/3, 6/4, 5/5, and so on.

For example, in some embodiments, a nucleic acid is added and the nucleic acid undergoes at least one nucleic acid modification or hybridization reaction. In some embodiments, the nucleic acid modification or hybridization reaction comprises nucleic acid synthesis or amplification. In some embodiments, the nucleic acid modification or hybridization reaction comprises hybridizing a probe to the nucleic acid to form a hybridized complex. In some embodiments, the method further comprises detecting the hybridized complex or nucleolysis of the probe.

Unless otherwise specified, concentrations of reagents in a solution or reconstituted composition can be for example, 0.0% (an omitted reagent), 0.001%, 0.004%, 0.008%, 0.0012%, 0.0016%, 0.0020%, 0.0030%, 0.0040%, 0.0050%, 0.0060%, 0.0080%, 0.01%, 0.02%, 0.04%, 0.06%, 0.1%, 0.2%, 0.3%, 0.4%, 0.5%, 0.6%, 0.8%, 1%, 2%, 3%, 4%, 5%, and the like. Also provided are reagents that are at "about" the above concentrations, less than the above concentrations, more than the above concentrations, ranges involving any two of the above concentrations.

Automated sampling handling equipment can be used to perform steps discussed above, such as adding reconstitution liquid to a solid composition on a plasma-treated surface. In some embodiments, additional substances such as a sample or template, enzyme, or salt is added using automated sampling handling equipment simultaneously with or sequentially following reconstitution. Reaction mixtures can be assembled, and reactions can be carried out in automated sampling handling equipment. In some embodiments, the automated sampling handling equipment is a robotic device with pipetters, mixers, incubators, and wash stations, such as a device capable of conducting simultaneous multiple assays, for example, PCR reactions, transcription mediated amplification, and target capture hybridization, such as the Hologic® Panther instrument (Hologic, Inc., MA).

Where one or more enzymes are present, the essential absence of inorganic salts can reduce loss of enzyme activity and formation of byproducts during storage of bulk reagents before drying, during short term storage of dried composition before sealing, and long term storage after sealing. In some embodiments, enzyme activity after all storage is at least 99% of the value before immediately prior to initiating storage, at least 98%, at least 95%, at least 90%, at least 80%, at least 75%, at least 70%, at least 60%, at least 50%, at least 40%, at least 30%, at least 20%, and ranges borded by these percentages, of the value prior to initiating storage, or alternatively, to the value of a comparator sample stored under optimal conditions.

Stability of compositions can be assessed after reconstitution of a dried product, e.g., from activity (i.e., rate or yield of amplification) or formation of byproducts. Lack of stability can result from loss of activity or formation of byproducts during storage either before or after drying. Activity or formation of byproducts can be absolute or relative measures. If relative, the base line for comparison can be a bulk reagent mixture before drying and reconstitution or a control reconstituted mixture differing from that under test in a defined way (e.g., presence of a salt of $Mg^{2+}$ or another salt). Activity can be assesed by rate of real time amplification or final yield of amplication product or hit rate. Sideproducts can be assayed by one or more of gel electrophoresis, a gel scanner, agarose gels, capillary electrophoresis, and so on.

The activity of a reconstituted amplifcation mixture (corrected if necessary for any differences due to a different volume of reconstitution) is preferably within 75, 80, 85, 90, or 95% or is indistinguishable within experimental error from that of the bulk reagent before drying. The side products present within a reconstituted amplification mixture (corrected if necessary for any differences due to a different volume of reconstitution) are preferably less than 20, 15, 10, 5, 4, 3, 2 or 1% by weight or average moles of the original compounds present in the bulk reagent before drying. Sometimes side products are below a limit of detection.

The solid compositions described above can be provided in a kit. Such a kit can contain the dried compositions in a vessel, such as a tube. In some embodiments, the kit contains a multiwell plate comprising two or more wells. Some kits contain a plurality of dried compositions supplied in separate vessels. Some kits include one or more multiwell plates including multiple dried compositions in two or more sealed well members of the multiwell plates.

Some kits also include a reconstitution liquid in a separate vessel from dried compositions. The reconstitution liquid can be provided in bulk for dispensing aliquots into individual vessels containing solid compositions or can be provided in the form of one or more unit dosages, each for combination with a single vessel containing a solid composition.

Optionally a vessel containing solid composition and a vessel containing reconstitution liquid can be separated by a frangible material. The frangible material can comprise aluminum foil, polypropylene, polyester, polyvinylchloride (PVC), or polyethylene. The frangible material can include one, two, three or more layers, each layer having the same composition, or each layer having a different composition, such as a foil layer in contact with a PVC layer. Films can be acquired from, e.g., Dow Chemical Co., Midland, MI or Arkema, Inc., King of Prussia, PA Piercing of the frangible material allows the reconstitution liquid to contact the solid (e.g., lyophilized) composition.

The kit can be designed to fit into a thermocycler or into an incubator so that enzymatic reactions take place directly in a compartment of the kit to avoid need to transfer compositions to different reaction vessel or containers holding such vessels.

Kits can be adapted for introduction of a a user-supplied reagent into a vessel within the kit, for example, by way of a port, a hose, a syringe puncturing a septum (see, US2014/0121515 and US2014/0276356), or alternatively, the user-supplied reagents, such as a nucleic acid template, can be mixed with reagents of the disclosure in a user-supplied container. One or more of the compartments of the kit can be supplied in an empty state and used as a mixing chamber.

All ranges include the whole and partial numbers of the range, with the understanding that partial numbers refers to ranges wherein a partial number makes sense. By way of example only, a nucleobase length range for a type of oligonucleotide would not include partial numbers as is makes no sense to refer to a partial nucleotide unit, wherein a temperature length range will include partial numbers as temperature measurements can be partial values. Moreover, ranges include the values defining the ranges.

EXAMPLES

Materials and Methods

Multiwell plastic cartridges were subjected to plasma treatment using a corona discharge in air or $O_2$ using commercial plasma treatment equipment such as an IoN 140 plasma chamber. The extent of plasma treatment was monitored by contact angle measurement. Untreated microplates had contact angles typically ranging from 75° to 100°. The treated microplates typically showed contact angles ranging from 11° to 22°. Thus, the plasma treatment decreased the contact angle by about 55° to 90°. The type of plastic in the cartridges was cyclic olefin copolymer.

Aqueous solutions containing trehalose (about 0.15 M to about 0.40 M) were dispensed into untreated and plasma-treated cartridge wells in volumes of about 15 to about 50 µl per well. In different runs, the solution was lyophilized using different cycle lengths, e.g., consistent with parameters provided above. Shorter cycles are generally preferred, so as to provide higher throughput, unless considerations such as solute concentration or lability of the product being lyophilized favor a longer cycle. As noted above, optimal lyophilization parameters are product-dependent. Solid compositions (pellets) of lyophilized trehalose were formed in the wells of the microplates and cartridges.

Adhesion of the pellets to the untreated and plasma-treated cartridge well surfaces was evaluated by performing drop testing as follows.

Each cartridge to be tested was placed on a sled held at a height of 120 mm over soft foam. The sled was released and allowed to fall onto the foam. The cartridge wells were checked for whether any pellets had become loose. These steps were repeated at successively increasing heights of 240, 360, and 440 mm for drops 2-4. Following the 440 mm drop onto the soft foam, the soft foam was replaced with a firm cushion, and drops 5-8 were performed from heights of 120, 240, 360, and 440 mm, with observation of whether any pellets had become loose after each drop. Following the 440 mm drop onto the firm cushion, the firm cushion was replaced with a hard surface (concrete or steel) and drops 9-32 were performed at a height h according to the formula $h = 20\ mm \times (d-8)$, where d is the drop number. E.g., drop 9 was from 20 mm, drop 10 was from 40 mm, and so on up to drop 32, which was from 480 mm Drops 33-98 were each performed from 480 mm onto the hard surface.

Example 1. Plasma Treatment with Short-Cycle Lyophilization

Figure 2A:
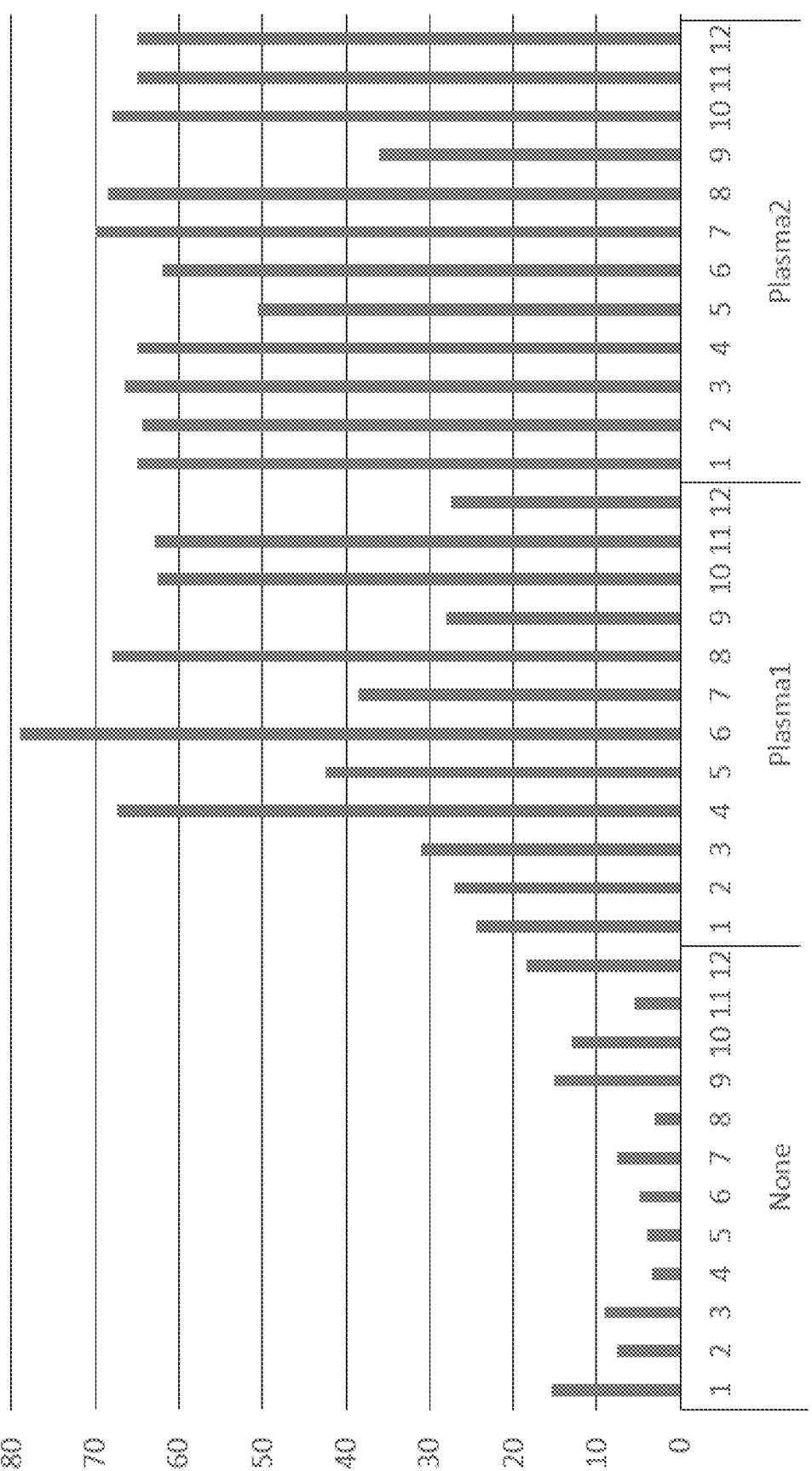
FIGS. 2A-2B show drop testing results for lyophilized pellets in untreated and plasma-treated wells as described in Example 1. Bar height indicates the number of drops before adhesion was disrupted.
Figure 2B:
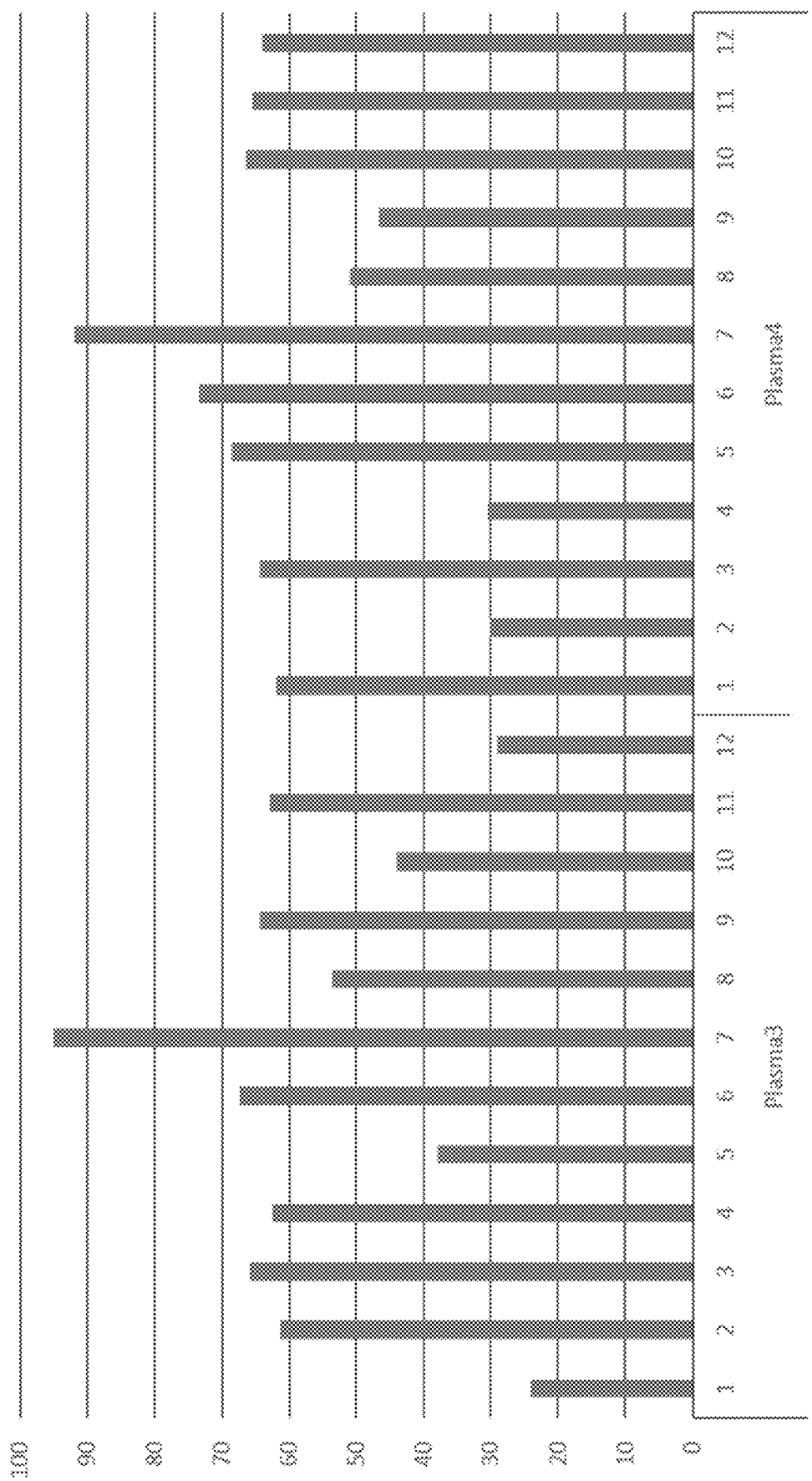

FIGS. 2A-2B show bar graphs in which the height of the each bar indicates the number of drops withstood before a pellet became loose in twelve wells each of an untreated cartridge ("None"), or four plasma-treated cartridges ("Plasma1" through "Plasma4"). Lyophilization was performed using a shorter cycle.

The adhesion of pellets to the wells was noticeably stronger in the plasma-treated wells. In the untreated wells, the pellets became loose following an average of 9.1 drops, while for the Plasma1, Plasma2, Plasma3, and Plasma4 treated wells, the pellets became loose following an average of 46.6, 62.2, 55.7, and 59.4 drops. respectively.

Additional experiments were performed using cartridges treated with plasma in air and $O_2$. In these experiments, the pellets became loose following an average number of drops between 74 and 88 (data not shown).

Example 2. Plasma Treatment with Long-Cycle Lyophilization

Figure 3A:
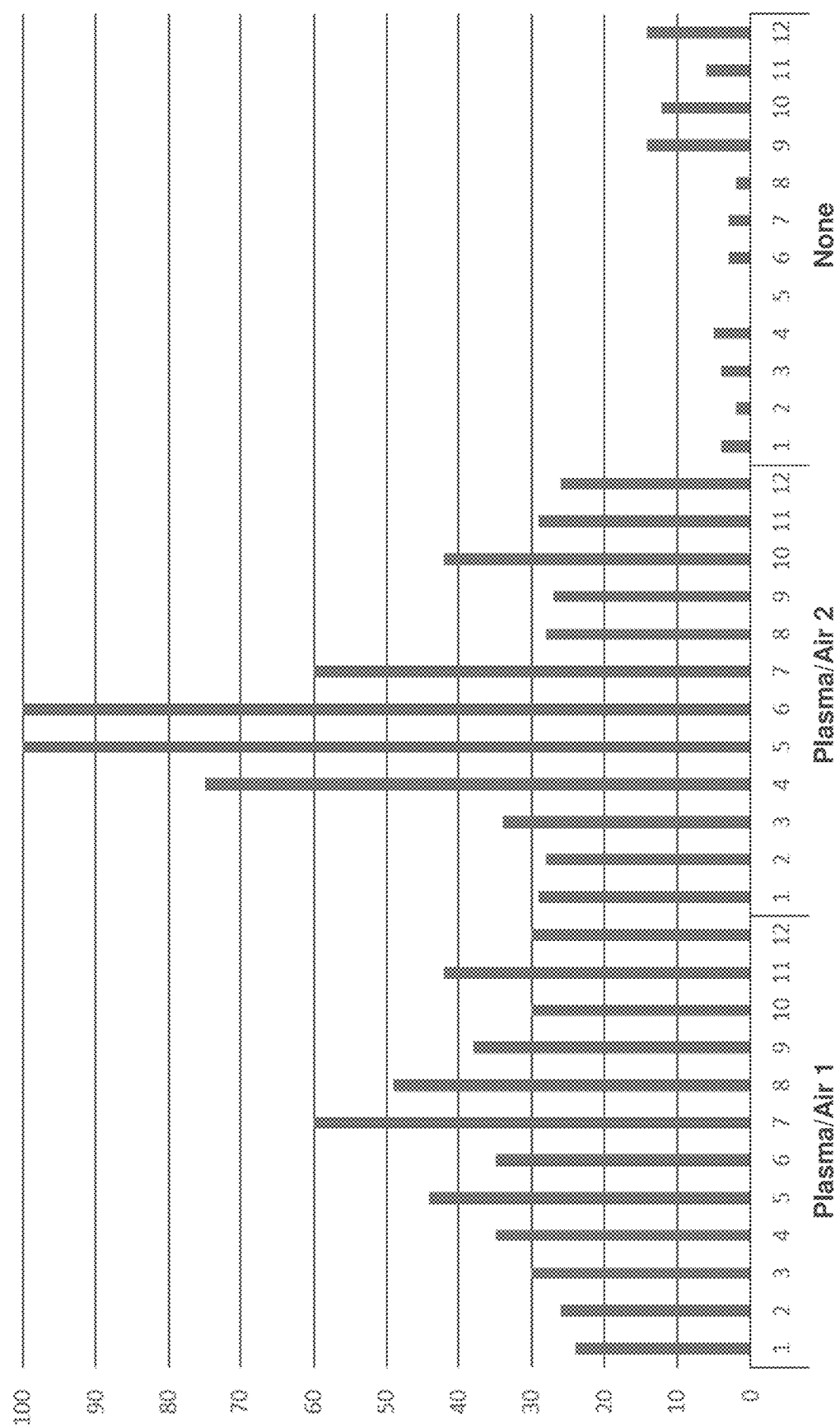
FIGS. 3A-3B show drop testing results for lyophilized pellets in untreated and plasma-treated wells as described in Example 2. Bar height indicates the number of drops before adhesion was disrupted.
Figure 3B:
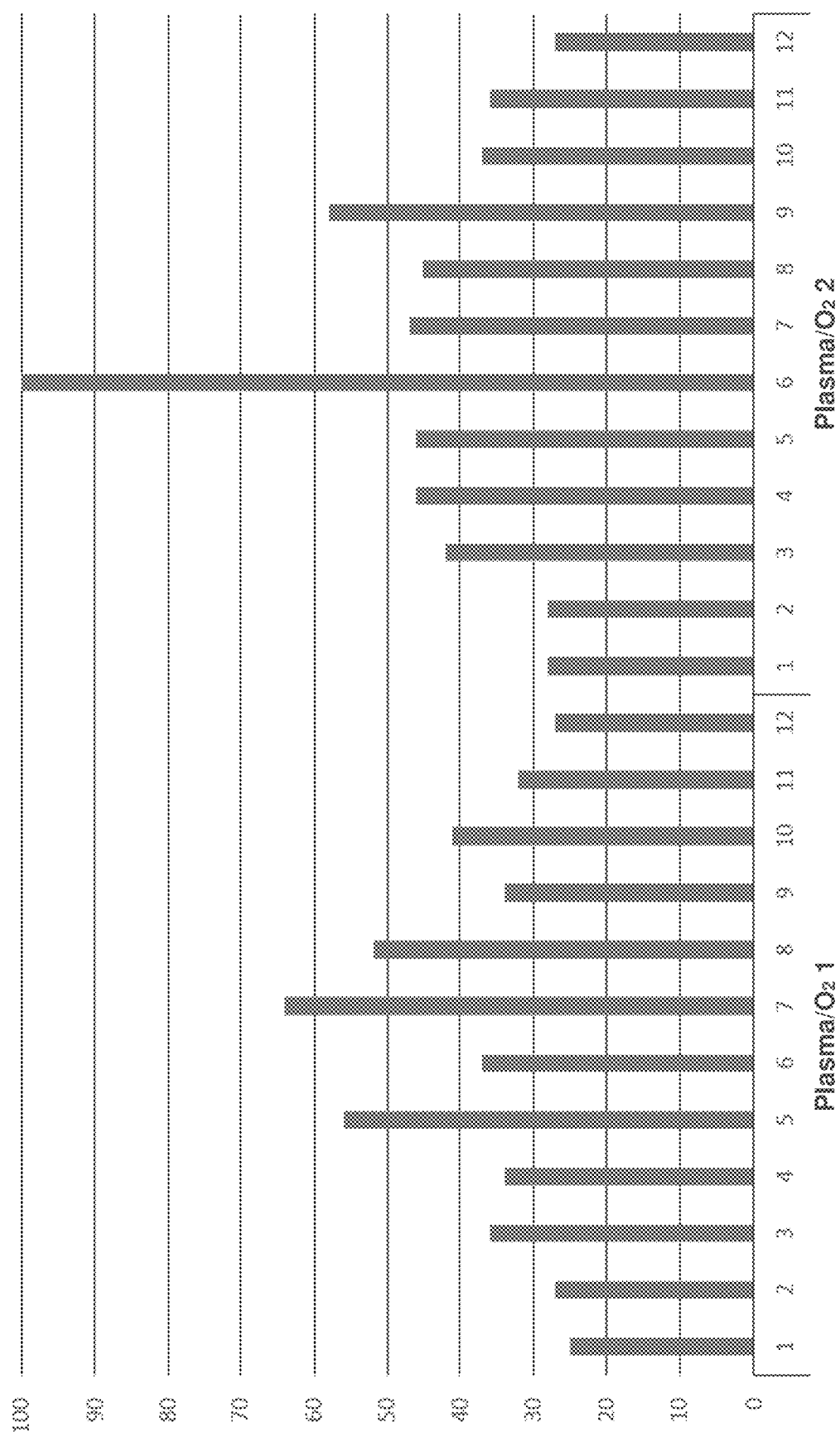

FIGS. 3A-3B show bar graphs in which the height of the each bar indicates the number of drops withstood before a pellet became loose in twelve wells each of an untreated cartridge ("None"), two cartridges treated with plasma in air ("Plasma/Air 1" and "Plasma/Air 2"), and two cartridges treated with plasma in $O_2$ ("Plasma/$O_2$ 1" and "Plasma/$O_2$ 2"). Lyophilization was performed using a longer cycle.

The adhesion of pellets to the wells was noticeably stronger in the plasma-treated wells. In the untreated wells, the pellets became loose following an average of 12.5 drops, while for the Plasma/Air 1, Plasma/Air 2, Plasma/$O_2$ 1, Plasma/$O_2$ 2 treated wells, the pellets became loose following an average of 36.9, 48.2, 38.8, and 45.0 drops, respectively.

Cartridges subjected to the Plasma1, Plasma2, Plasma3, and Plasma4 treatments as in Example 1 were filled with trehalose solution and lyophilized using a longer cycle. The pellets became loose following an average number of drops between 35 and 41 (data not shown).

Example 3. Plasma-Treated Cartridge Storage

Cartridges were subjected to plasma treatment as in Example 1. Following plasma treatment, the cartridges were stored in an oxygen containing environment for a period of time of either 1-day, 30-days, 90-days or 100-days. At the end of the storage period, wells in the cartridge were filled with a saccharide containing PCR reaction solution and the solution was lyophilized. Control cartridges that were not plasma-treated were also filled with the saccharide solution, lyophilized and stored for each of 1-day, 30-days, 90-days, and 100-days.

Following lyophilization, all of the cartridges containing lyophilized substances were subjected to package performance testing, which is designed to emulate shipping and handling conditions. The individual tests performed were (i) Initial Manual Handling, ASTM D5276-98 Standard, Schedule A, (ii) Stacked Vibration, ASTM D4728-06 Standard, Schedule D, (iii) Loose Load Vibration, ASTM D999-08 Standard, Schedule F, (iv) Concentrated Impacts, ASTM D6344-04 Standard, Schedule J, and (v) Final Manual Handling, ASTM D5276-98 Standard, Schedule A. Following testing, each cartridge containing the lyophilized substance was visually inspected and was used in a PCR assay (reconstituted, combined with a target nucleic acid, and subjected to amplifying and detecting conditions). Plasma-treated cartridges, regardless of storage time, contained uniformly shaped dried compositions adhered to the bottom of the cartridge wells, while untreated cartridges contained broken and dislodged compositions. PCR assay performance for the substances in the plasma treated cartridges provided robust, uniform target detection results without any false negatives, whereas the PCR assay performance for the substances in the untreated cartridges were inconsistent and included a number of false negatives.

Plasma treated cartridges that are stored in a non-inert atmosphere (such as being stored in the presence of oxygen) for at least 100-days, retain intact and fully active lyophilized substances following shipping and distribution, while untreated cartridges do not.

The present disclosure is not to be limited by compositions, reagents, methods, diagnostics, laboratory data, and the like of the present disclosure, and that the present disclosure is not be limited by any particular or preferred embodiments that are disclosed herein.

What is claimed is:

1. A solid composition adhered to a plasma-treated surface, wherein the plasma-treated surface is an interior surface of a vessel, wherein the solid composition has a mass from about 600 micrograms to about 20 grams, wherein the solid composition is in the form of a lyophilized pellet adhered to the plasma-treated interior surface, wherein the solid composition is macroscopic in three orthogonal dimensions, such that the solid composition is not a coating and has a length, a width, and a height of greater than 1 mm, and wherein the solid composition is sufficiently adhered to remain substantially attached to the plasma-treated surface following a package performance test in which the plasma-treated surface containing the solid composition is dropped from a height of about 20 mm to about 1000 mm onto a substrate.

2. The solid composition of claim 1, wherein the solid composition comprises a bulking agent and at least one of an enzyme and an oligonucleotide.

3. The solid composition of claim 1, wherein the plasma-treated surface comprises plastic.

4. The solid composition of claim 3, wherein the plastic comprises at least one of a polyethylene, polyethylene terephtalate, polypropylene, polymethacrylate, polyvinyl chloride, polystyrene, polyolefin, polycarbonate, polyurethane, starch-derived plastic, or cyclic olefin copolymer.

5. The solid composition of claim 2, wherein the bulking agent comprises a saccharide, glycine, or hydroxyethyl starch.

6. The solid composition of claim 2, wherein the bulking agent comprises a saccharide comprising at least one of sucrose, mannitol, raffinose, or trehalose.

7. The solid composition of claim 1, wherein the vessel comprises a tube having a volume ranging from about 40 ul to about 60 ml.

8. The solid composition of claim 1, wherein the vessel is a multiwell plate comprising a plurality of wells.

9. The solid composition of claim 1, wherein the solid composition has a mass ranging from about 5 mg to about 20 g, about 200 mg to about 20 g, about 1 g to about 20 g, about 5 g to about 20 g, about 5 mg to about 1 g, about 5 mg to about 500 mg, about 5 mg to about 200 mg, about 5 mg to about 100 mg, about 5 mg to about 50 mg, about 5 mg to about 20 mg, about 5 mg to about 10 mg, about 10 mg to about 200 mg, about 20 mg to about 200 mg, about 50 mg to about 200 mg, or about 100 mg to about 200 mg.

10. The solid composition of claim 1, wherein the solid composition comprises one or more enzymes.

11. The solid composition of claim 10, wherein the one or more enzymes include at least one of a DNA polymerase, an RNA polymerase, a ligase, a kinase, a phosphatase, a protease, an exonuclease, and an endonuclease.

12. The solid composition of claim 1, wherein the solid composition comprises a buffer.

13. The solid composition of claim 1, wherein the solid composition comprises a salt.

14. The solid composition of claim 1, wherein the solid composition is free of inorganic salt or has an inorganic salt concentration of 5 mM or less.

15. The solid composition of claim 1, wherein the solid composition comprises at least one oligonucleotide useful for performing a molecular assay.

16. The solid composition of claim 1, wherein the solid composition comprises one or more nucleoside triphosphates.

17. The solid composition of claim 1, wherein the solid composition contains a single unit dose of amplification or detection reagents.

18. The solid composition of claim 1, wherein the solid composition contains a pharmaceutically active agent.

19. The solid composition of claim 1, wherein the plasma-treated surface is a surface comprising a polyolefin and has a contact angle of 5° to 50°.

20. The solid composition of claim 1, wherein the plasma-treated surface is a surface comprising a polyolefin and has a surface energy from 33 to 55 dynes/cm.

21. The solid composition of claim 1, wherein the plasma-treated surface is a surface comprising a polyethylene or polypropylene and has a surface energy from 35 to 55 dynes/cm.

22. The solid composition of claim 1, wherein the plasma-treated surface is a surface treated with a cold cathode discharge, hollow cathode discharge, DC-induced discharge, radio frequency (RF)-induced discharge, corona discharge, glow discharge, or charged particle beam.

23. The solid composition of claim 1, wherein the plasma-treated surface is a surface treated with a corona discharge at a watt density ranging from about 25 watt/min/m2 to about 2000 watt/min/m2, about 50 watt/min/m2 to about 1500 watt/min/m2, about 100 to about 1200 watt/min/m2, about 200 to about 1000 watt/min/m2, about 100 to about 600 watt/min/m2, or about 200 watt/min/m2 to about 600 watt/min/m2 or, wherein the surface was treated with a corona discharge at a watt density ranging from about 25 watt/min/m2 to about 2000 watt/min/m2, about 50 watt/min/m2 to about 1500 watt/min/m2, about 100 to about 1200 watt/min/m2, about 200 to about 1000 watt/min/m2, about 100 to about 600 watt/min/m2, or about 200 watt/min/m2 to about 600 watt/min/m2.

* * * * *